United States Patent
Akama et al.

(10) Patent No.: US 11,391,736 B2
(45) Date of Patent: Jul. 19, 2022

(54) ANALYTE DETECTION METHOD

(71) Applicant: SYSMEX CORPORATION, Kobe (JP)

(72) Inventors: Kenji Akama, Kobe (JP); Hiroyuki Noji, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 16/536,743

(22) Filed: Aug. 9, 2019

(65) Prior Publication Data

US 2020/0049704 A1 Feb. 13, 2020

(30) Foreign Application Priority Data

Aug. 10, 2018 (JP) .............................. JP2018-152016

(51) Int. Cl.
*G01N 33/543* (2006.01)
(52) U.S. Cl.
CPC . *G01N 33/54386* (2013.01); *G01N 33/54306* (2013.01); *G01N 33/54313* (2013.01)
(58) Field of Classification Search
CPC ....... G01N 33/54386; G01N 33/54306; G01N 33/54313; G01N 33/54353; G01N 33/54373; G01N 33/00; G01N 33/5302; G01N 33/543; G01N 33/54326; G01N 33/54346; G01N 33/582; G01N 33/58; G01N 21/645; G01N 21/6452; G01N 2021/6482
See application file for complete search history.

(56) References Cited

U.S. PATENT DOCUMENTS 10,725,048 B2 * 7/2020 Akama ................. G01N 33/68
2013/0345088 A1 12/2013 Noji et al.

FOREIGN PATENT DOCUMENTS

| JP | 2013-503352 A | 1/2013 |
| JP | 2013-533469 A | 8/2013 |
| WO | 2011/053894 A2 | 5/2011 |
| WO | 2011/053894 A3 | 9/2011 |
| WO | 2011/109364 A2 | 9/2011 |
| WO | 2015/120147 A1 | 8/2015 |
| WO | 2015/195404 A1 | 12/2015 |

(Continued)

OTHER PUBLICATIONS

S.P. Mulvaney et al: "Rapid, femtomolar bioassays in complex matrices combining microfluidics and magnetoelectronics", Biosensors and Bioelectronics, Elsevier Science Ltd. UK, Amsterdam, NL, vol. 23, No. 2, Sep. 16, 2007, pp. 191-200, ISSN 0956-5663; Cited in the extended European search report dated Dec. 2, 2019 in a counterpart European patent application.

(Continued)

*Primary Examiner* — Tracy Vivlemore
*Assistant Examiner* — Nam P Nguyen
(74) *Attorney, Agent, or Firm* — Sughrue Mion, PLLC

(57) ABSTRACT

Disclosed is an analyte detection method, including detecting an analyte in such a state that a complex composed of the analyte in a sample of interest, a particle capable of bonding to the analyte and a trapping substance capable of bonding to the analyte is formed on a substrate, wherein the analyte is detected on the basis of an index associated with a behavior of the particle.

16 Claims, 16 Drawing Sheets

(56) References Cited

FOREIGN PATENT DOCUMENTS

WO 2018/081440 A1 5/2018

OTHER PUBLICATIONS

Kenji Akama et al: "Wash- and Amplification-Free Digital Immunoassay Based on Single-Particle Motion Analysis", ACS Nano, Nov. 4, 2019, ISSN 1936-0851; Cited in the extended European search report dated Dec. 2, 2019 in a counterpart European patent application.
Extended European search report dated Dec. 2, 2019 in a counterpart European patent application No. 19190906.8.
Jonathan Silver et al., "Tethered-bead, immune sandwich assay", Biosensors and Bioelectronics, 2015, pp. 117-123, vol. 63.
Kenji Akama et al., "Droplet-Free Digital Enzyme-Linked Immunosorbent Assay Based on a Tyramide Signal Amplification System", Analytical Chemistry, 2016, pp. 7123-7129, vol. 88.
Communication pursuant to Article 94(3) EPC dated Oct. 15, 2020 in a counterpart European patent application No. 19190906.8.
Communication pursuant to Article 94(3) EPC dated Sep. 13, 2021 in a counterpart European patent application No. 19190906.8.
The Japanese Office Action dated Apr. 12, 2022 in a counterpart Japanese patent application No. 2018-152016.

\* cited by examiner

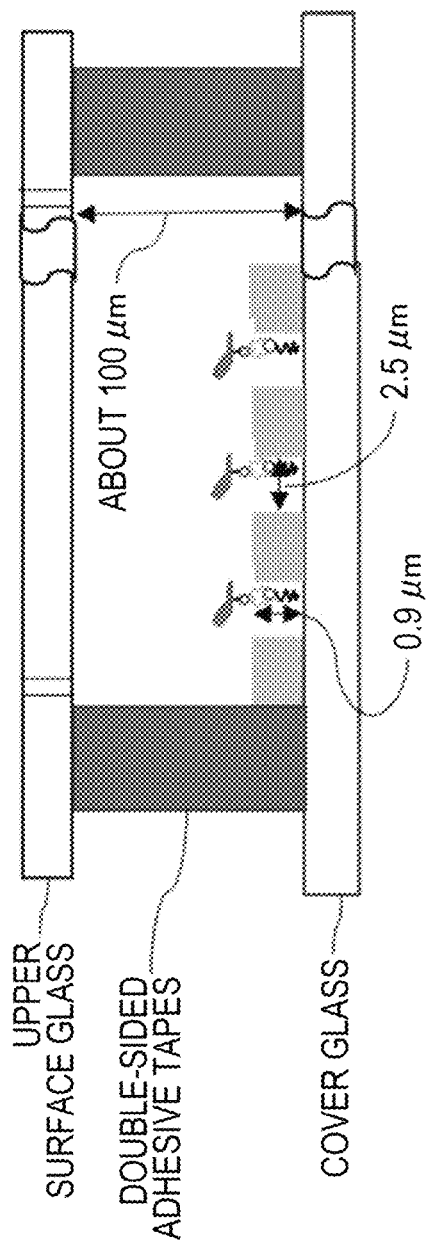
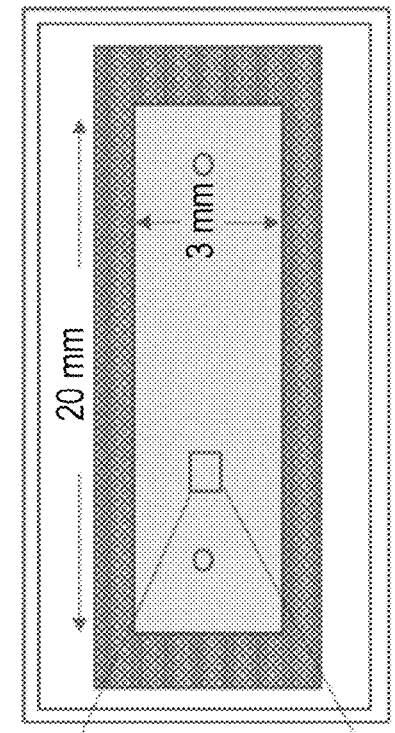
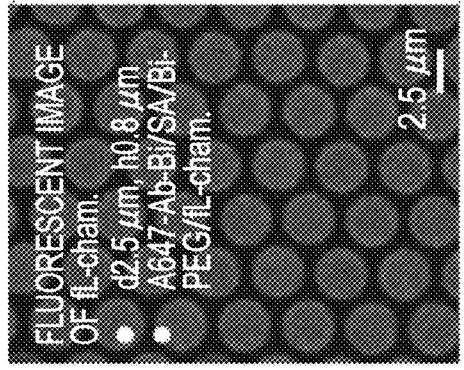
FIG. 7

ANALYTE DETECTION METHOD

CROSS REFERENCE TO RELATED APPLICATIONS

This application claims priority from prior Japanese Patent Application No. 2018-152016, filed on Aug. 10, 2018, entitled "ANALYTE DETECTION METHOD", the entire contents of which are incorporated herein by reference.

TECHNICAL FIELD

The present invention relates to an analyte detection method and others.

BACKGROUND

Heretofore, a detection technique utilizing a bonding reaction specific to an analyte is known. For example, the technique disclosed in WO2011/109364 is a so-called digital ELISA method, in which the analyte is quantified by trapping each of molecules of an analyte by a trapping substance, then separating the trapped molecules of the analyte individually in a plurality of compartments, and then determining the number of the compartments.

However, this detection technique usually requires such a complicated process that a substance immobilized on a solid phase is separated from a substance non-immobilized on the solid phase (i.e., B/F separation). Furthermore, even when the B/F separation is performed, non-specific adsorption still remains. In this case, the non-specific adsorption interferes as signal background, and consequently the analyte cannot be detected in a specific manner disadvantageously.

SUMMARY

The scope of the present invention is defined solely by the appended claims, and is not affected to any degree by the statements within this summary.

The present inventors have made intensive and extensive studies in view of the above-mentioned problems. As a result, it is found that the problems can be solved by an analyte detection method, including detecting an analyte in such a state that a complex composed of the analyte in a sample of interest, a particle capable of bonding to the analyte and a trapping substance capable of bonding to the analyte is formed on a substrate, wherein the analyte is detected on the basis of an index associated with a behavior of the particle. The present inventors have made more extensive and intensive studies on the basis of this finding, and the present invention has been accomplished.

The present invention includes the following aspect.

A. An analyte detection method, comprising detecting an analyte in such a state that a complex comprising the analyte in a sample of interest, a particle capable of bonding to the analyte and a trapping substance capable of bonding to the analyte is formed on a substrate, wherein the analyte is detected on the basis of an index associated with a behavior of the particle.

B. An analyte detection method, comprising steps of:
forming on a substrate a complex comprising an analyte in a sample of interest, particle capable of bonding to the analyte and a trapping substance capable of bonding to the analyte, and
detecting the analyte on the basis of at least one index selected from the group consisting of a mean square displacement, a diffusion coefficient (D) and an average velocity (V) of the Brownian motion of the particle.

C. An analyte detection method, comprising steps of:
forming on a substrate a complex comprising an analyte in a sample of interest, particle capable of bonding to the analyte and a trapping substance capable of bonding to the analyte,
taking a still image of the behavior of the particle or a moving image of the behavior of the particle,
calculating using the still image or the moving image at least one index selected from the group consisting of a mean square displacement, a diffusion coefficient (D) and an average velocity (V) of the Brownian motion of the particle, and
detecting the analyte by determining that a particle of which the index is equal to or less than the threshold value of the upper limit of the index or a particle of which the index is equal to or less than the threshold value of the upper limit of the index and is equal to or more than the threshold value of the lower limit of the index is a particle to which the analyte is bonded.

D. An analyte detection device, equipped with a processing unit which, in such a state where a complex including an analyte in a sample of interest, a particle capable of bonding to the analyte and a trapping substance capable of bonding to the analyte is formed on a substrate, can calculate an index associated with a behavior of the particle from an image showing the behavior of the particle,
wherein it is determined that a particle of which the index falls within a specified range is a particle to which the analyte is bonded.

BRIEF DESCRIPTION OF THE DRAWINGS

FIG. 7 is a schematic diagram showing the antibody linker-modified fL chamber array flow cell produced in Example 1-1. In the plan view of the flow cell, "Fluorescent image" is an image in which a fluorescent dye is linked to an antibody and based on which it is confirmed that only the inside of a chamber is modified with the antibody. In the test in Example 1-3, an antibody to which a fluorescent dye is not linked is used;

DETAILED DESCRIPTION OF THE PREFERRED EMBODIMENTS

Figure 1:
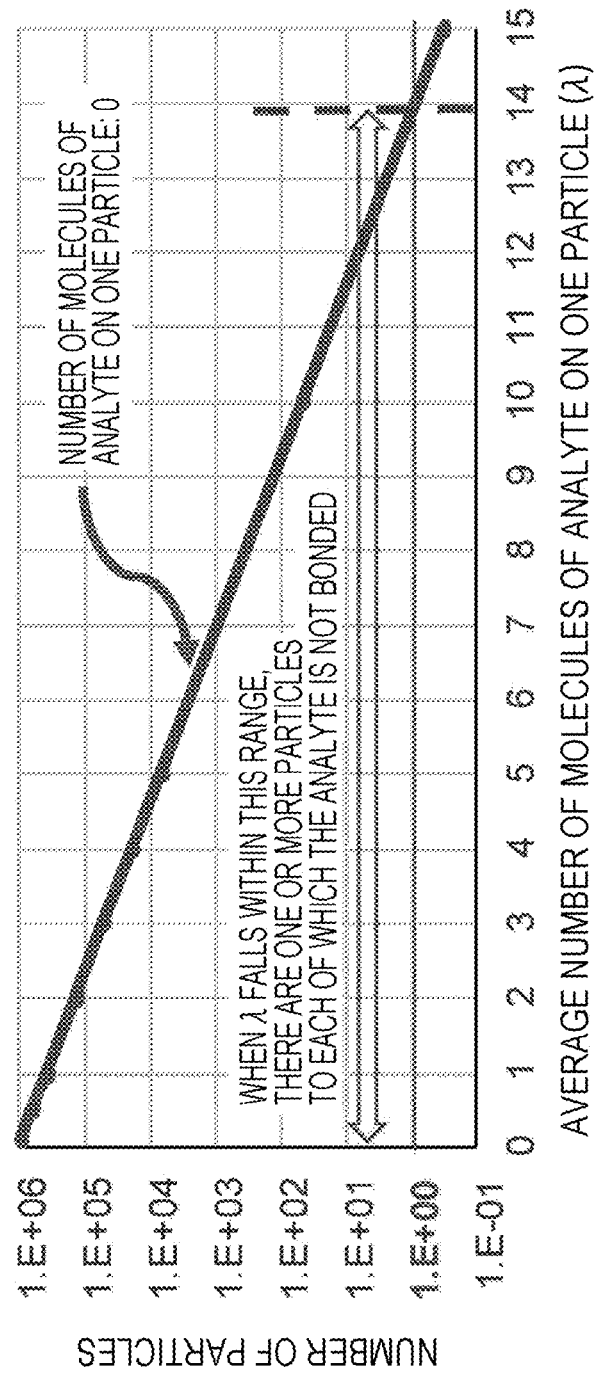
FIG. 1 is a graph showing that, in the case where the number of particle is $10^6$, at least one statistically significant particle is not bonded to an analyte when the particles are contacted in such a manner that the requirement represented by the formula: $\lambda < 14$ is satisfied.

In the description, the terms "including" and "include" as used herein include the concepts of "containing", "contain", "is substantially composed of" and "is only composed of".

1. Detection Method

In one aspect, the present disclosure relates to an analyte detection method, including detecting an analyte in such a state that a complex composed of the analyte in a sample of interest, a particle capable of bonding to the analyte and a trapping substance capable of bonding to the analyte is formed on a substrate, wherein the analyte is detected on the basis of an index associated with a behavior of the particle (in the description, the method is sometimes referred to as a "detection method according to the present disclosure). Hereinbelow, the method will be described.

<1-1. Sample of Interest>

The sample of interest is not particularly limited, as long as an analyte is contained. Examples of the sample include: a biological sample, such as blood, plasma, serum, lymph fluid and a cell or tissue lysate; an excretion, such as urine and feces; and an environmental sample, such as river water, seawater and soil.

The sample may include only one type of sample, or may include a combination of two or more types of samples.

<1-2. Analyte>

The analyte is a substance to be detected by the detection method according to the present disclosure, and may be any one as long as there is a substance having bonding affinity for the analyte (in the description, the substance is also referred to as a "bondable substance") or the bondable substance can be produced. In the case where the bondable substance is an antibody, any substance having antigenicity can be used as the analyte. Specific examples of the analyte include an antibody, a protein, a nucleic acid, a polysaccharide, a biologically active substance, a vesicle, a bacterium, a virus, a polypeptide, a hapten, a therapeutic agent, and a metabolite of a therapeutic agent.

The polypeptide is not particularly limited with respect to the number of amino acid residues therein, and includes a protein having a relatively large number of amino acid residues as well as a so-called peptide or oligopeptide which is a polypeptide having relatively small number of amino acid residues.

The polysaccharide includes a polysaccharide composed of only sugar chains as well as a sugar chain bonded to another molecule, e.g., a sugar chain occurring on the surface of a cell or a protein and a lipopolysaccharide that is an outer membrane component of a bacterium.

Examples of the biologically active substance include a cell proliferation factor, a differentiation induction factor, a cell adhesion factor, an enzyme, a cytokine, a hormone, a sugar chain and a lipid.

The vesicle is not particularly limited, as long as the vesicle is a vesicle composed of a membrane. The vesicle includes a vesicle in which a liquid phase is not contained, a vesicle in which a liquid phase is contained, a vesicle in which a mixed phase composed of a liquid phase and an oily phase is contained, a vesicle in which smaller vesicles are contained, and the like. Examples of the vesicle include: an extracellular vesicle such as an exosome, a microvesicle and an apoptotic body; and an artificial vesicle such as a liposome.

The analyte may include only one type of analyte, or may include a combination of two or more types of analytes.

<1-3. Particle>

The particle is not particularly limited, as long as the particle has bondability to the analyte, is movable in a liquid, and can be visualized by itself or can be visualized upon the reaction with another substance. The particle is preferably a particle that enables Brownian motion in a liquid. The particle preferably has bondability specific to the analyte.

The material for the particle is not particularly limited. Examples of the material include: a metal-made particle such as a particle of gold, silver, copper, iron, aluminum, nickel, manganese, titanium, or an oxide of any one of these metals; a resin-made particle such as a polystyrene particle and a latex particle; and a silica particle. The shape of the particle is not particularly limited. Examples of the shape include a spherical shape, a rectangular parallelepiped shape, a cubic shape, a three-sided pyramid-like shape, and a shape similar to any one of these shapes. It is preferred that the particle have, on the surface thereof, a substance for further enhancing and/or further increasing the bonding of other substances (e.g., a bondable substance 1 as mentioned below). Examples of the substance include: a substance having a reactive group such as an epoxy group, an amino group, a carboxy group and an azide group; and a substance having affinity for another molecules, such as avidin, protein A and protein B. From the viewpoint that an external force as mentioned below can be applied more easily, the particle is preferably a magnetic particle, a charged particle or the like. The term "charged particle" refers to an electrically charged particle. The material for the particle is not particularly limited, as long as the material is any one of those mentioned above and can apply an electric charge.

The average particle size of the particle is preferably 1 μm or less, more preferably 700 nm or less, from the viewpoint that the Brownian motion of the particle in a liquid can be detected more easily. The average particle size is preferably 1 nm to 10 µm, more preferably 10 nm to 10 µm, still more preferably 50 nm to 10 µm, from the viewpoint, for example, that the particle can be visualized by magnification with a microscope or the like. From the above-mentioned two viewpoints, the average particle size is preferably 1 nm to 1 µm, more preferably 10 nm to 1 µm, still more preferably 50 nm to 1 µm, still more preferably 50 nm to 700 nm. The average particle size of the particle is a volume median diameter as measured by a laser diffraction-scattering method using a particle size distribution measurement device. An example of the particle size distribution measurement device is "Microtrac MT3000II" manufactured by Nikkiso Co., Ltd. The term "particle size" as used herein refers to a diameter.

The wording "having bondability to" or "capable of bonding to" refers to the ability to bond to an analyte reversibly or irreversibly. The force to be needed for the bonding is not particularly limited, and includes a hydrogen bond, an electrostatic force, a van der Waals force, a hydrophobic bond, a covalent bond and a coordinate bond. The degree of the bondability is not particularly limited. For example, the dissociation constant between the analyte and the particle is $1 \times 10^{-4}$ to $1 \times 10^{-16}$ M, $1 \times 10^{-6}$ to $1 \times 10^{-14}$ M, $1 \times 10^{-8}$ M to $1 \times 10^{-13}$ M, or $1 \times 10^{-9}$ to $1 \times 10^{-12}$ M.

The particle-bonding site in the analyte may be the same as or different from the below-mentioned site at which the trapping substance is bonded (wherein, when the particle-bonding site is different from the below-mentioned site, both of a case where the particle-bonding site overlaps the trapping substance-bonding site and a case where the particle-bonding site does not overlap the trapping substance-bonding site are included). In the case where the analyte is a monomer, it is preferred that the particle-bonding site is different from the trapping substance-bonding site, and it is more preferred that the particle-bonding site is a site which is different from the trapping substance-bonding site and does not overlap the trapping substance-bonding site. In the case where it is intended to detect an analyte having a plurality of same bonding sites, such as a polymeric analyte, the particle-bonding site may be the same as or different from the trapping substance-bonding site. For example, in the case where each of the particle and the trapping substance contains an antibody and the analyte is a monomeric antigen, it is preferred that an epitope for the analyte to which the particle is bonded is different from an epitope for the analyte to which the trapping substance is bonded. Alternatively, in the case where each of the particle and the trapping substance contains a nucleic acid and the analyte is a nucleic acid, it is preferred that an analyte-bonding nucleotide sequence in the analyte is different from a trapping substance-bonding nucleotide sequence in the analyte.

In the description, the term "antibody" includes: an immunoglobulin, such as a polyclonal antibody, a monoclonal antibody and a chimeric antibody; and a fragment including a variable region of the immunoglobulin, such as a Fab fragment, a F(ab')2 fragment, a Fv fragment, a minibody, scFv-Fc, scFv, a diabody, a triabody and a tetrabody.

In the description, the term "nucleic acid" includes DNA and RNA, as well as known chemically modified nucleic acids as exemplified as follows. For example, in order to prevent the decomposition of a nucleic acid with a hydrolysis enzyme such as nuclease, a phosphate residue in each nucleotide may be substituted by a chemically modified phosphate residue such as phosphorothioate (PS), methyl phosphonate and phosphorodithioate. It may also be possible to substitute a hydroxyl group at position-2 in a sugar moiety (ribose) in each ribonucleotide by a group —OR (wherein R represents, for example, $CH_3$ (2'-O-Me), $CH_2CH_2OCH_3$ (2'-O-MOE), $CH_2CH_2NHC(NH)NH_2$, $CH_2CONHCH_3$, $CH_2CH_2CN$ or the like). Furthermore, a base moiety (e.g., pyrimidine, purine) may be chemically modified. For example, it is possible to introduce a methyl group or a cationic functional group to position-5 in a pyrimidine base or substitute a carbonyl group at position-2 by a thiocarbonyl group. Furthermore, it is also possible to modify a phosphoric acid moiety or a hydroxyl moiety with, for example, biotin, an amino group, a lower alkylamine group, an acetyl group or the like. However, the chemical modification is not limited to these ones. The term "nucleic acid" includes a naturally occurring nucleic acid, as well as a BNA (Bridged Nucleic Acid), a LNA (Locked Nucleic Acid) and a PNA (Peptide Nucleic Acid). The term "nucleic acid" includes both of a monomer and a polymer.

The particle preferably contains a "bondable substance 1" which is capable of bonding to the analyte by itself, more preferably has the bondable substance 1 immobilized on the surface thereof. The bondable substance 1 may have various forms depending on the type of the analyte, and various types of the bondable substances 1 may be employed for the same analyte. For example, in the case where the analyte is a substance having antigenicity, an antibody against the substance can be used as the bondable substance 1. In the case where the analyte is an antibody, an antigen can be used as the bondable substance 1. In the case where the analyte is a nucleic acid, a nucleic acid capable of forming a strand complementary to the nucleic acid can be used as the bondable substance 1. In the case where the analyte is a receptor or a ligand, a ligand or a receptor can be used, respectively, as the bondable substance 1. Therefore, specific examples of the bondable substance 1 include an antibody, an antigen, a nucleic acid, a receptor, a ligand capable of bonding to a receptor and an aptamer. In addition, a low-molecular-weight compound capable of bonding to a specific molecule (e.g., biotin) can also be used as the bondable substance 1. Only one type of the bondable substance 1 may be used, or a combination of two or more types of the bondable substances 1 may be used.

The particle may contain a labeling substance, such as a fluorescent substance (e.g., fluorescein, rhodamine, Texas red, tetramethylrhodamine, carboxyrhodamine, phycoerythrin, 6-FAM (trademark), Cy (registered trademark) 3, Cy (registered trademark) 5, Alexa Fluor (registered trademark) series), an enzyme (e.g., β-galactosidase, alkaline phosphatase, glucose oxidase, peroxidase, polyphenol oxidase). Only one type of the labeling substance may be used, or a combination of two or more types of the labeling substances may be used.

Only one type of particle or particles may be used, or a combination of two or more types of particles may be used.

<1-4. Trapping Substance>

The trapping substance is not particularly limited, as long as the trapping substance has bondability to the analyte and is immobilized on the substrate. The trapping substance may include a single molecule or a complex of a plurality of molecules. The trapping substance preferably has bondability specific to the analyte.

With respect to the wording "capable of bonding to" or "having bondability", the same explanation as that mentioned regarding to the particle can apply.

The trapping substance preferably contains a "bondable substance 2" that has bonding affinity for the analyte by itself. With respect to the bondable substance 2, the same explanation as that mentioned regarding to the bondable substance 1 can apply.

The trapping substance can contain a substance that can be utilized for the immobilization onto the substrate. Examples of the substance include a protein, an antibody, an antigen, a nucleic acid, a receptor, a ligand capable of bonding to a receptor, an aptamer and a low-molecular-weight compound. Only one type of the substance may be used, or a combination of two or more types of the substances may be used.

From the viewpoint that the behavior of the particle can be detected more easily, it is preferred that the trapping substance contains a linker. The linker is not particularly limited, as long as the linker can link the substrate to a substance having bondability to the analyte. The "substance that can be utilized for the immobilization onto the substrate" may also be used as the linker. Examples of the linker include a nucleic acid, a polymeric substance and a lipid. Examples of the nucleic acid include DNA and RNA. An example of the polymeric substance is a synthetic polymer (preferably a water-soluble polymer) such as poly(ethylene glycol). An example of the lipid is an MPC polymer. Among these compounds, a synthetic polymer, a lipid and the like are preferred, and a lipid is more preferred.

The length of the linker is not particularly limited, as long as the Brownian motion of the particle cannot be restricted. The length depends on the height of a space containing the substrate, and is up to a length determined by subtracting the particle size of the particle from the height of the space. The lower limit of the length is preferably 15 nm, more preferably 30 nm, still more preferably 50 nm. The upper limit of the length is preferably 8/10, more preferably 5/10, still more preferably 2/10, of the height of the space that contains the substrate.

The wording "immobilized onto the substrate" means an immobilized state through the direct or indirect bonding to the substrate. The immobilization of the trapping substance onto the substrate can be carried out by a conventional method or a method similar to the conventional method. Specific form of immobilization is not particularly limited, and includes immobilization through a covalent bond, immobilization through the bonding of avidin or streptavidin to biotin, immobilization through physical adsorption, and the like. In the case where the substrate is blocked by BSA or the like, the trapping substance may be immobilized onto the substrate through the blocking agent.

Only one type of the trapping substance may be used, or a combination of two or more types of the trapping substances may be used.

<1-5. Substrate>

The substrate is not particularly limited, as long as the trapping substance can be immobilized onto a part or the entire area of the substrate (i.e., a solid phase). An example of the substrate is a substrate containing, as the main component thereof, a plastic material such as polystyrene, a glass, nitrocellulose or the like. In one aspect, the substrate includes a layer that serves as a base and another layer arranged on a part or the whole area of the layer. The shape of the substrate is not particularly limited, as long as a place where the analyte, the particle and the trapping substance can come in contact with one another (e.g., a liquid phase) can be kept. Examples of the shape of the substrate include a shape formed from only flat surfaces such as sheet-like surfaces, a semi-spherical shape, a shape formed only from curved surfaces such as tubular surfaces, and a shape formed from a combination of two or more of these shapes.

In one aspect, the substrate constitutes a space of which at least a part is surrounded by the substrate (the space is sometimes simply referred to as a "space", hereinafter). It is preferred that the substrate constitutes a chamber in which the analyte, the particle and the trapping substance are contained. For example, in one preferred aspect, a chamber composed of a side surface and a bottom surface is formed on the substrate. In one preferred aspect, the substrate includes a plurality of the chambers. Each of the chambers may include one particle or a plurality of particles. In one preferred aspect, one particle is included in one chamber.

The depth (or height) of the chamber is preferably five times or less the particle size of the particle. More specifically, the depth is preferably 10 μm or less, more preferably 5 μm or less, still more preferably 2 μm or less, further more preferably 1 μm or less. The lower limit of the depth is, for example, 0.2 μm, 0.4 μm, 0.6 μm or 0.8 μm.

The width (or diameter when the bottom surface has a round shape) of the space is not particularly limited. When it is supposed that one particle is arranged in one chamber, the width can be adjusted appropriately depending on the particle size. In this case, the width may be about 1.05 to 5 times the particle diameter, for example. Specific examples of the width of the space include 20 mm or less, 1 mm or less, 50 μm or less, 10 μm or less, and 5 μm or less. The lower limit of the width is, for example, 0.5 μm, 1 μm or 2 μm. The sensitivity of the detection of the analyte can be increased by decreasing the volume of the space. The formation of the chamber can be carried out by a conventional method or a method similar to the conventional method. For example, the chamber can be formed by the method mentioned in a known publication document (US 2013/0345088 A1) or a method similar to the method. The entire contents of US 2013/0345088 A1 are incorporated herein by reference.

<1-6. Formation of Complex>

The complex includes an analyte, a particle having bondability to the analyte, and a trapping substance having bondability to the analyte. More specifically, the trapping substance, the analyte and the particle are arranged in this order in the complex as observed from the substrate side.

The method for forming the complex on the substrate preferably includes the following step:

bringing an analyte in a sample of interest, a particle capable of bonding to the analyte, a trapping substance capable of bonding to the analyte and a substrate into contact with one another to form a complex on the substrate.

More preferably, the method for forming the complex on the substrate includes:

a particle contact step of bringing an analyte in a sample of interest into contact with particles each capable of bonding to the analyte in such a manner that some of the particles can be bonded to the analyte to form analyte-bonded particles and at least one of the particles which is statistically significant cannot be bonded to the analyte; and a complex formation step of bringing the sample that had been subjected to the particle contact step into contact with a substrate onto which a trapping substance capable of bonding to the analyte is immobilized, thereby forming a complex of the analyte-bonded particles and the trapping substance on the substrate.

In the particle contact step and the complex formation step, the "contact" is usually carried out in a solution. The solution is generally a solution in which water is the main solvent. The solution is, for example, a buffer solution. Examples of the buffer solution include a phosphate buffer solution, phosphate-buffered physiological saline, a Tris buffer solution, a HEPES buffer solution, a borate buffer solution, an acetate buffer solution and a citrate buffer solution. The solution may contain various additives, as long as the bonding among the analyte, the particle and the trapping substance cannot be interfered significantly.

The mode of the "contact" in the particle contact step is not particularly limited. Typically, the contact can be carried out by simply mixing a sample containing the analyte with the particle. The contact time is, for example, 10 seconds to 3 hours, preferably about 1 minute to 2 hours.

The mode of the "contact" in the complex formation step is not particularly limited, either. Typically, the contact can be carried out by introducing a sample obtained by the particle contact step into a space at least partially surrounded by the substrate. In this case, in order to accelerate the contact of the particle with the substrate, it is preferred to apply an external force capable of causing the particle to move in a direction toward the substrate. After the introduction of the sample obtained by the particle contact step to the space, it is preferred that the upper surface of the space is filled with a hydrophobic solvent. The filling can be carried out by a conventional method or a method similar to the conventional method. The contact time may vary depending on the present or absence of the application of the external force. In the case where the external force is applied, a shorter contact time (e.g., about 10 seconds to 5 minutes) may be employed.

The external force is a force capable of drawing the particle to the substrate side. The type of the external force is not particularly limited. A proper external force can be selected regardless the type of the particle or depending on the type of the particle. Examples of the external force include a magnetic force, a coulomb force, a centrifugal force, a fluid force, light and ultrasonic waves, preferably a magnetic force, a coulomb force and ultrasonic waves. With respect to the combination of the type of the particle and the external force, it is preferred to employ a magnetic force when the particle contains a magnetic particle, and it is preferred to employ a coulomb force when the particle contains a charged particle. Only one type of external force may be employed, or a combination of two or more types of external forces may be employed.

In the particle contact step, it is desirable to bring into contact "in such a manner that some of the particles can be bonded to the analyte to form analyte-bonded particles and at least one statistically significant particle among the particles cannot be bonded to the analyte" (also simply referred to as a "manner", hereinafter), from the viewpoint of the quantification performance. More specifically, the manner is such a manner that, when an analyte in a sample of interest is brought into contact with $10^6$ particles each capable of bonding to the analyte, the average number ($\lambda$) of the molecules of the analyte on the particle, which can be determined in accordance with the equation shown below, satisfies the requirement represented by the formula: $\lambda < 14$.

$$\lambda = [AbL]/[Beads] \quad \text{[Mathematical formula 1]}$$

($\lambda$: Average number of molecules of analyte on particle, [AbL]: concentration of complex of analyte and antibody, [Beads]: concentration of particles)

The value of $\lambda$ can be controlled by varying the conditions under which a sample containing an analyte is to be brought into contact with particles each capable of bonding to the analyte, and $\lambda$ can be determined from the concentration of the analyte in the sample, the amount of the sample and the number of the particles to be contacted. For example, in the case where the number of the particles is $10^6$, the analyte is brought into contact with the particles in such a manner that the requirement represented by the formula: $\lambda < 14$ can be satisfied. In this case, at least one statistically significant particle among the particles is not bonded to the analyte (see FIG. 1).

<1-7. Detection>

The detection of the analyte can be carried out on the basis of an index associated with a behavior of the particle. The behavior is preferably a behavior associated with the Brownian motion of the particle.

The behavior of the particle can be observed under the conditions where the presence of the particle can be detected as an optical signal. For example, in the case where the particle has a certain size, the behavior of the particle can be observed by magnification (wherein any one of a bright-field image and a dark-field image may be employed). In the case where the label is a fluorescent substance, the behavior of the particle can be observed under the conditions where the fluorescence coming from the substance can be detected. In the case where the label is an enzyme, the behavior of the particle can be observed under the conditions where emission and/or fluorescence coming from the substance can be detected. The behavior of the particle can be observed by taking a still image and/or a moving image by means of a proper imaging means under the above conditions. The imaging means is not particularly limited, as long as a still image or a moving image can be taken. Examples of the imaging means include a CCD and a CMOS. With respect to a still image, the exposure time is not particularly limited. The still image may be taken employing a relatively long exposure time.

The index is not particularly limited, as long as the index is associated with a behavior (e.g., a momentum) of a particle. A still image showing a behavior of the particle or a moving image of the particle is obtained, and then the index is determined on the basis of the still image or the moving image. Examples of the index (behavior pattern) that can be determined on the basis of the still image or the moving image include a moving distance of a particle, a moving speed of a particle, an area of a region in the image in which a particle appears, and a shape of a trail drawn by a particle on the image.

The index is preferably an index associated with the momentum of each particle at a specified point of time, from the viewpoint that the behavior can be known more accurately. As the index, an averaged index is preferred. Examples of the averaged index include a mean square displacement, a diffusion coefficient (D) and an average velocity (V). These indexes can be calculated by a known method on the basis of an observation image (e.g., a moving image, a successive still image) of a behavior of a particle.

Only one type of index may be employed, or a combination of two more types of indexes may be employed.

Figure 2:
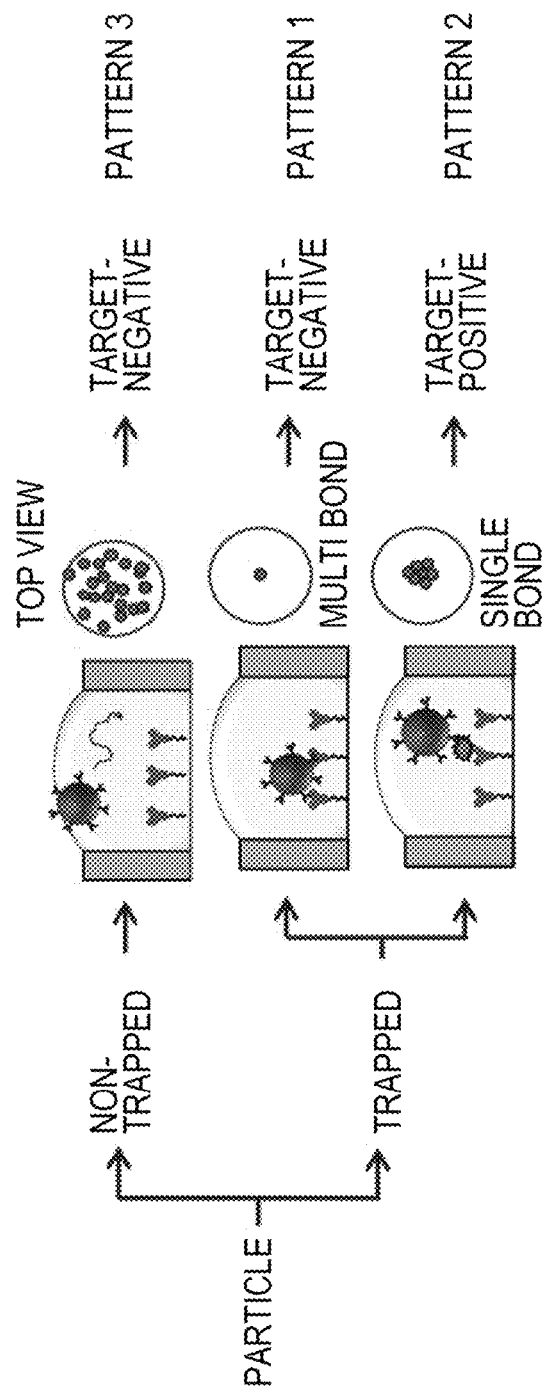
FIG. 2 is a diagram showing three patterns into which the particles are classified based on a behavior thereof after the formation of a complex.
Figure 13:
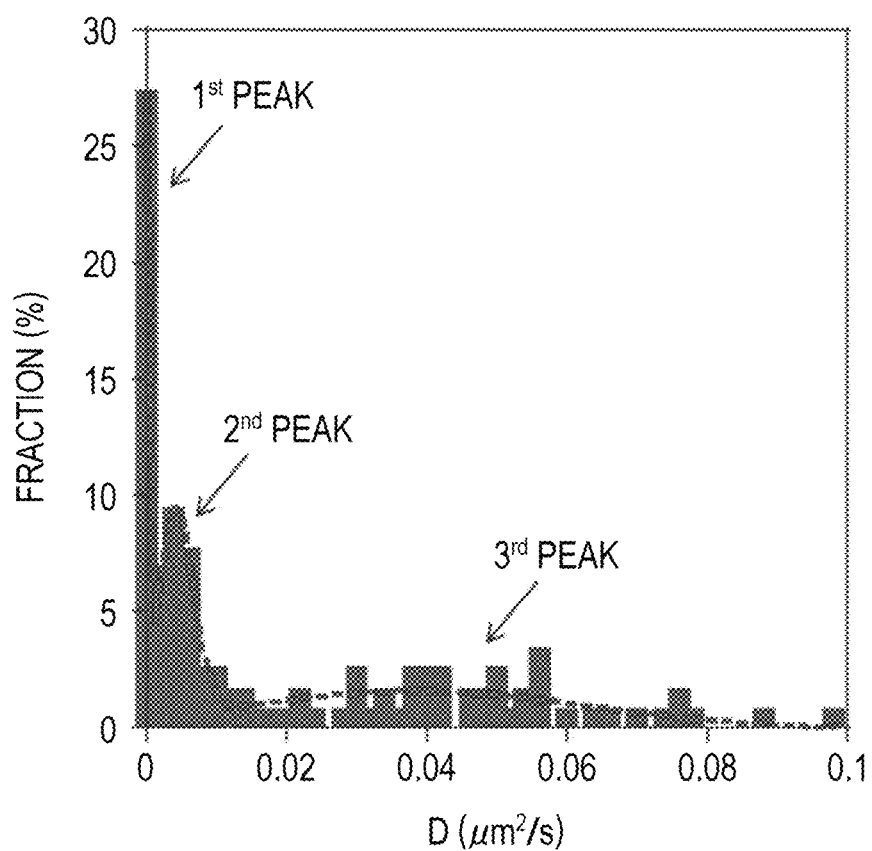
FIG. 13 is a graph showing the result of the distribution of the diffusion coefficient (D) of the observed particle by calculating the diffusion coefficient (D) from a tilt until 0.02 second in accordance with Formula 2 in Example 1-3-4.

After the formation of the complex, the behavior pattern of the particle can be roughly classified into three patterns (FIG. 2, FIG. 13). A pattern in which the index value associated with a behavior is extremely small (pattern 1 in FIG. 2, a pattern of 1st peak in FIG. 13) shows a state where the Brownian motion is restricted and a particle almost remains still on the substrate. In this case, it is considered that the particle is a particle relying on a non-specific bonding (usually multi-point bonding) in which an analyte does not intervene. A pattern in which the index value associated with a behavior is large (pattern 3 in FIG. 2, a pattern of 3rd peak in FIG. 13) shows a state where the Brownian motion occurs in a free state without bonding to a trapping substance (i.e., without forming a complex). A pattern in which the index value associated with a behavior is medium (pattern 2 in FIG. 2, a pattern for 2nd peak in FIG. 13) shows a state where an analyte-bonded particle and an antibody on a substrate, which serves as a trapping substance, are bonded to each other through an antigen-antibody reaction and, as a result, a motion (particularly, Brownian motion) occurs. For these reasons, the analyte can be detected on the basis of an index associated with a behavior.

In one preferred aspect of the present disclosure, the analyte can be detected by comparing a behavior pattern determined from a still image or a moving image with a predetermined behavior pattern of a complex containing the analyte (i.e., a reference behavior pattern 1) and determining whether or not the determined behavior pattern coincides with the reference behavior pattern 1. Namely, when it is determined that the determined behavior pattern coincides with the reference behavior pattern 1, it is determined that a particle showing the determined behavior pattern is a particle to which the analyte is bonded. In a more preferred aspect, it is possible to add a step of comparing the determined behavior pattern with a predetermined behavior pattern of a complex that does not contain the analyte (i.e., a reference behavior pattern 2) and determining whether or not the determined behavior pattern coincides with the reference behavior pattern 2. In this case, when it is determined that the determined behavior pattern does not coincide with the reference behavior pattern 2, it is determined that a particle showing the determined behavior pattern is a particle to which the analyte is bonded. The method for determining whether or not the patterns coincide with each other is not particularly limited. For example, the determination on whether or not the patterns coincide with each other can be carried out by performing pattern matching by image analysis. Alternatively, the determination can also be carried out utilizing an artificial intelligence.

In one preferred aspect of the present disclosure, the step of detecting the analyte includes a step of determining that a particle of which the index associated with a behavior of the particle falls within a specified range is a particle to which the analyte is bonded. The "specified range" is not particularly limited, as long as the entire or a part of the pattern 1 and/or the pattern 3 can be eliminated.

More specifically, the step of detecting the analyte includes a step of, for example, determining that a particle of which the index associated with a behavior of the particle is equal to or less than the threshold value of the upper limit (pattern A) or a particle of which the index is equal to or less than the threshold value of the upper limit and is equal to or more than the threshold value of the lower limit (pattern B) is a particle to which the analyte is bonded. The upper limit is provided for the purpose of eliminating pattern 3 as much as possible, and the lower limit is provided for the purpose of eliminating pattern 1 as much as possible. When the determination is made based on the criterion that the index is equal to or less than the threshold value of the upper limit, it becomes possible to eliminate some or all of free particles (pattern 3) each of which is not bonded to a trapping substance (without forming a complex) without needing to perform B/F separation such as the washing of the substrate. When the determination is further made based on the criterion that the index is equal to or more than the threshold value of the lower limit in addition to the criterion associated with the upper limit, it becomes possible to eliminate some or all of non-specifically bonded particles (pattern 1) without needing to perform B/F separation such as the washing of the substrate.

The "specified range", the upper limit and the lower limit can be adjusted on the basis of reference values (e.g., a mean value, a median value, a peak value) for patterns 1 to 3. The value that can be employed as the upper limit is a value determined by subtracting a certain value (e.g., (SD value of pattern 3)×n (wherein n represents a numerical value more than 0, such as 20 or less, 10 or less, 5 or less, 2 or less, 1 or less; with respect to the variable n, the same rule applies to the followings)) from the reference value of pattern 3 or a value determined by adding the certain value to the reference value, a value determined by subtracting a certain value (e.g., (SD value of pattern 2)×n) from the reference value of pattern 2 or a value determined by adding the certain value to the reference value, or the like. The value that can be employed as the lower limit is a value determined by subtracting a certain value (e.g., (SD value of pattern 3)×n) from the reference value of pattern 1 or a value determined by adding the certain value to the reference value, a value determined by subtracting a certain value (e.g., (SD value of pattern 2)×n) from the reference value of pattern 2 or a value determined by adding the certain value to the reference value, or the like. With respect to pattern 2, a clear peak may not be obtained. In this case, the "specified range", the upper limit, the lower limit and the like can be adjusted on the basis of the reference value for pattern 1 and/or pattern 3. It is also possible to set the reference value itself as the upper limit and/or the lower limit. As each of these values, a value that is set in each case may be employed, or a value that is set when the detection is carried out previously under the same conditions may also be employed.

It is preferred that the step of detecting the analyte further includes a step of counting the number of particles to each of which the analyte is bonded and then quantifying the analyte on the basis of the result of the counting. In this regard, the concentration may be determined on the basis of a calibration curve. It is also possible to employ the ratio of a specific signal to all of signals (the sum total of specific signal and a non-specific signal) as the index of the content of the analyte.

2. Detection Device

In one aspect, the present disclosure relates to an analyte detection device equipped with a processing unit which, in such a state where a complex including an analyte in a sample of interest, a particle capable of bonding to the analyte and a trapping substance capable of bonding to the analyte is formed on a substrate, can calculate an index associated with a behavior of the particle from an image showing the behavior of the particle, wherein it is determined that a particle of which the index falls within a specified range is a particle to which the analyte is bonded (in the description, the device is also referred to as a "detection device according to the present disclosure"). Hereinbelow, the detection device according to the present disclosure will be described with reference to the drawings attached. However, the detection device according to the present disclosure is not limited to these embodiments. In the detection device according to the present disclosure, the explanations of the terms that are used for describing the detection method according to the present disclosure and are already described are omitted. However, the explanations about the terms used for describing the detection method according to the present disclosure can be also applied for describing the detection device according to the present disclosure.

<2-1. Configuration of Device>

Figure 3:
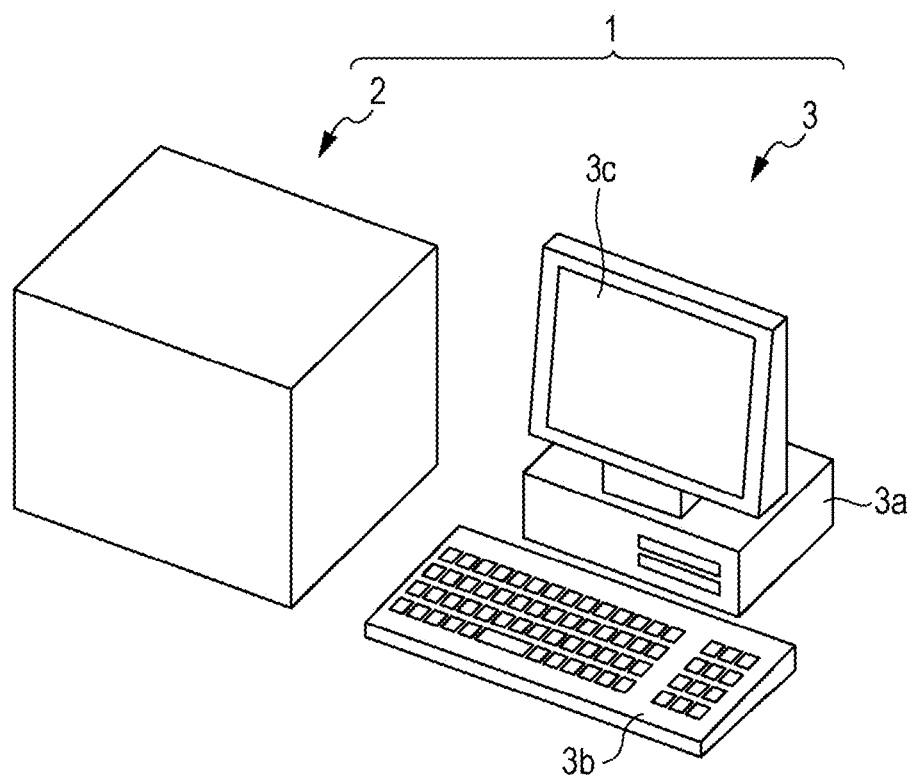
FIG. 3 is a schematic diagram showing the configuration of one embodiment of the detection device of the present invention.

The detection device according to the present disclosure is not particularly limited, as long as the processing unit is included. In a preferred aspect, the detection device according to the present disclosure is provided with a reaction unit and an imaging unit. In FIG. 3, a schematic view of one embodiment of a preferred aspect of the detection device according to the present disclosure is shown.

The detection device 1 shown in FIG. 3 includes a measurement device 2 provided with a reaction unit and an imaging unit. The reaction unit includes therein a reaction solution for forming a complex composed of an analyte in a sample of interest, a particle capable of bonding to the analyte and a trapping substance capable of bonding to the analyte on a substrate. The imaging unit can take an image of a behavior of the particle in the reaction unit. The optical information, e.g., an image showing the behavior of the particle, is sent to a computer system 3 including the processing unit.

As the measurement device 2, a microscope equipped with an imaging unit can be used. In this case, each chamber, e.g., a microchamber plate, to be mounted on a stage of the microscope can be served as the reaction unit.

The microscope is not particularly limited, as long as the microscope has a resolution power to such an extent that the individual particles can be recognized. A proper microscope may be selected depending on the type of the particle and the particle detection method to be employed. Specific examples of the microscope include: an optical microscope such as a stereo microscope, a fluorescence microscope, a laser scanning microscope and a confocal laser microscope; an electron microscope such as a transmission electron microscope and a scanning electron microscope; a scanning probe microscope such as an atomic force microscope, a scanning tunneling microscope and a scanning near field optical microscope; an X-ray microscope; and a scanning acoustic microscope.

The imaging unit is arranged at a position at which a microscopic observation image can be obtained, such as an eyepiece lens section, a phototube and a C mount. The imaging unit is not particularly limited, as long as a still image or a moving image can be taken. Examples of the imaging unit include a digital camera, an analogue camera, a digital video camera and an analogue video camera.

It is preferred that the detection device 2 is further equipped with an external force application unit. The external force application unit is arranged at a position at which an external force capable of applying an external force that can cause the particles to move in a direction toward the substrate can be applied. The manner to arrange the external force application unit may be selected appropriately by selecting the method for adjusting the external force appropriately. For example, in the case where the external force is adjusted by the approach of a magnet toward the substrate, a magnet that is movable as required (e.g., movable in the vertical direction and/or the horizontal direction) is arranged below the substrate. Alternatively, in the case where the external force is adjusted by adjusting the magnetic force of a magnet fixed below the substrate, a magnet of which the magnetic force can be adjusted by a current is arranged below the substrate. Alternatively, in the case where the external force is adjusted by adjusting the potential of an electrode, an electrode of which the potential can be adjusted by a current is arranged above and below the substrate in such a manner that the electrode can come into contact with a reaction solution placed in the reaction unit.

The detection device 1 shown in FIG. 3 also includes a computer system 3 that is equipped with a processing unit and is connected to the measurement device 2 directly or through a network.

In such a state where a complex including an analyte in a sample of interest, a particle capable of bonding to the analyte and a trapping substance capable of bonding to the analyte is formed on a substrate, the processing unit can calculate an index associated with a behavior of the particle from an image showing the behavior of the particle, wherein it is determined that a particle of which the index falls within a specified range is a particle to which the analyte is bonded.

The computer system 3 includes a computer main body 3a, an input device 3b and a display unit 3c that can display information about samples, results and the like. The computer system 3 can receive optical information such an image showing a behavior of the particle from the measurement device 2. A processor in the computer system 3 can calculate an index associated with a behavior of the particle on the basis of the image and can execute a program for identifying a particle to which the analyte is bonded.

Figure 4:
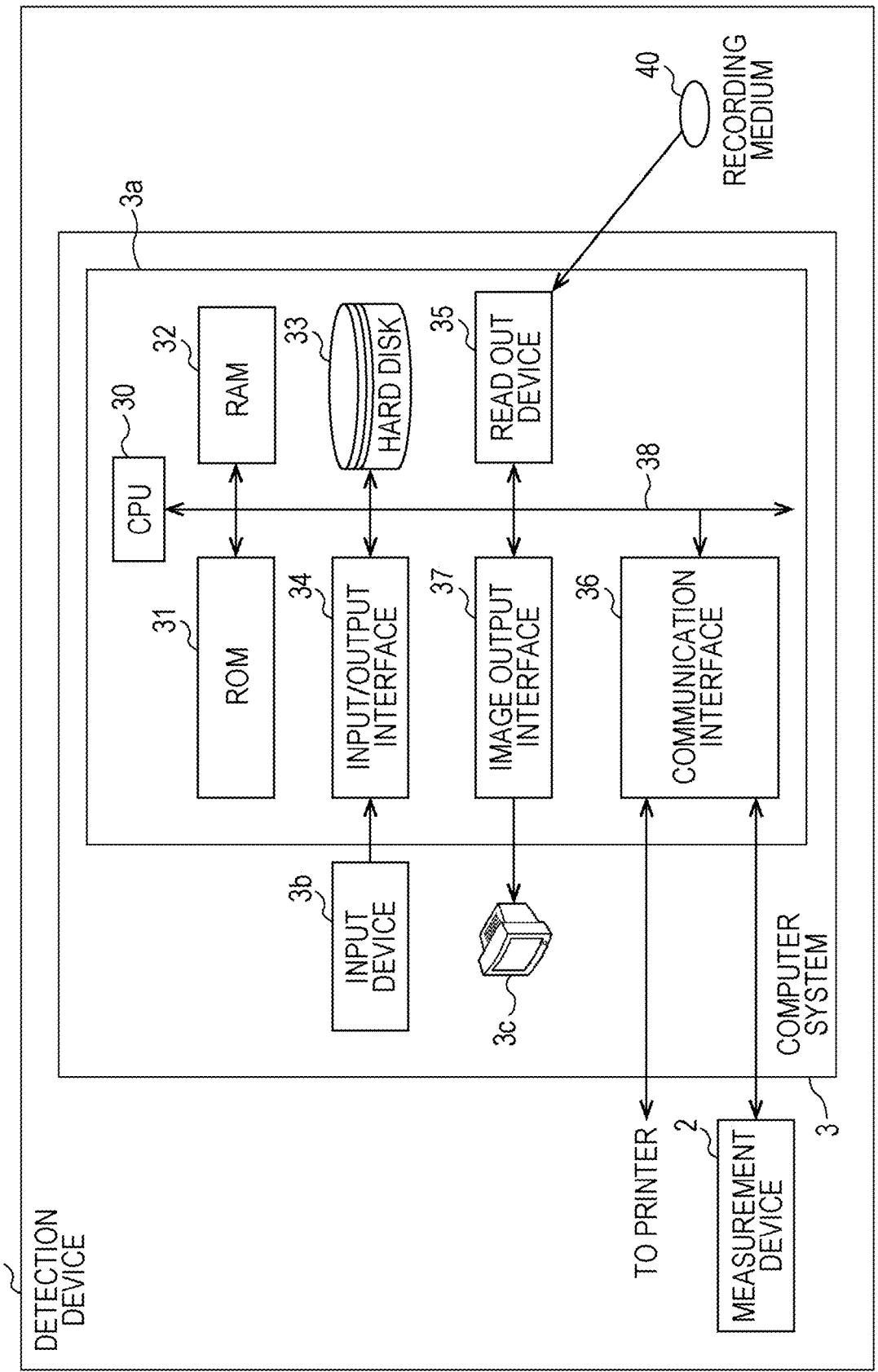
FIG. 4 is a block diagram showing the configuration of a hardware of the detection device shown in FIG. 3.

FIG. 4 is a block diagram showing the configuration of a hardware of the detection device shown in FIG. 3.

As shown in FIG. 4, the computer main body 3a is equipped with a processing unit (e.g., a CPU (Central Processing Unit)) 30, a ROM (Read Only Memory) 31, a RAM (Random Access Memory) 32, a hard disk 33, an input/output interface 34, a readout device 35, a communication interface 36, and an image output interface 37. The processing unit (CPU) 30, the ROM 31, the RAM 32, the hard disk 33, the input/output interface 34, the readout device 35, the communication interface 36 and the image output interface 37 are connected with one another in a data communicable manner through a bus 38.

The processing unit (CPU) 30 can execute a computer program stored in the ROM 31 and a computer program loaded in the RAM 32. When the processing unit (CPU) 30 executes an application program, the processing unit (CPU) 30 can act as a terminal which serves as an identification device for identifying a signal that indicates an analyte.

The ROM 31 is composed of a mask ROM, a PROM, an EPROM, an EEPROM and the like. In the ROM 31, a computer program that can be executed by the processing unit (CPU) 30 and data to be used for the computer program are recorded.

The RAM 32 is composed of a SRAM, a DRAM and the like. The RAM 32 is used for the read out of computer programs recorded on the ROM 31 and the hard disk 33. The RAM 32 can also be used as a working area for the processing unit (CPU) 30 upon the execution of these computer programs.

In the hard disk 33, an operating system that is to be executed by the processing unit (CPU) 30, a computer program such as an application program (e.g., a computer program for identifying a signal indicating an analyte), and data to be used for the execution of the computer program are installed.

The readout device 35 is composed of a flexible disk drive, a CD-ROM drive, a DVD-ROM drive and the like. The readout device 35 can read out a computer program or data recorded on a portable recording medium 40.

The input/output interface 34 is composed of, for example, a serial interface such as USB, IEEE1394 and RS-232C, a parallel interface such as SCSI, IDE and IEEE1284, and an analogue interface composed of a D/A converter and an A/D converter. To the input/output interface 34, an input device 3b such as a key board and a mouse is connected. An operator can input data to the computer main body 3a using the input device 3b.

An example of the communication interface 36 is Ethernet (registered trademark) interface. The computer system 3 can send print date to a printer through the communication interface 36.

The image output interface 37 is connected to the display unit 3c composed of LCD and CRT. Due to this configuration, the display unit 3c can output a video signal corresponding to image data obtained from the processing unit (CPU) 30. The display unit 3c can display an image (screen) in response to the input video signal.

<2-2. Operation of Device>

Figure 5:
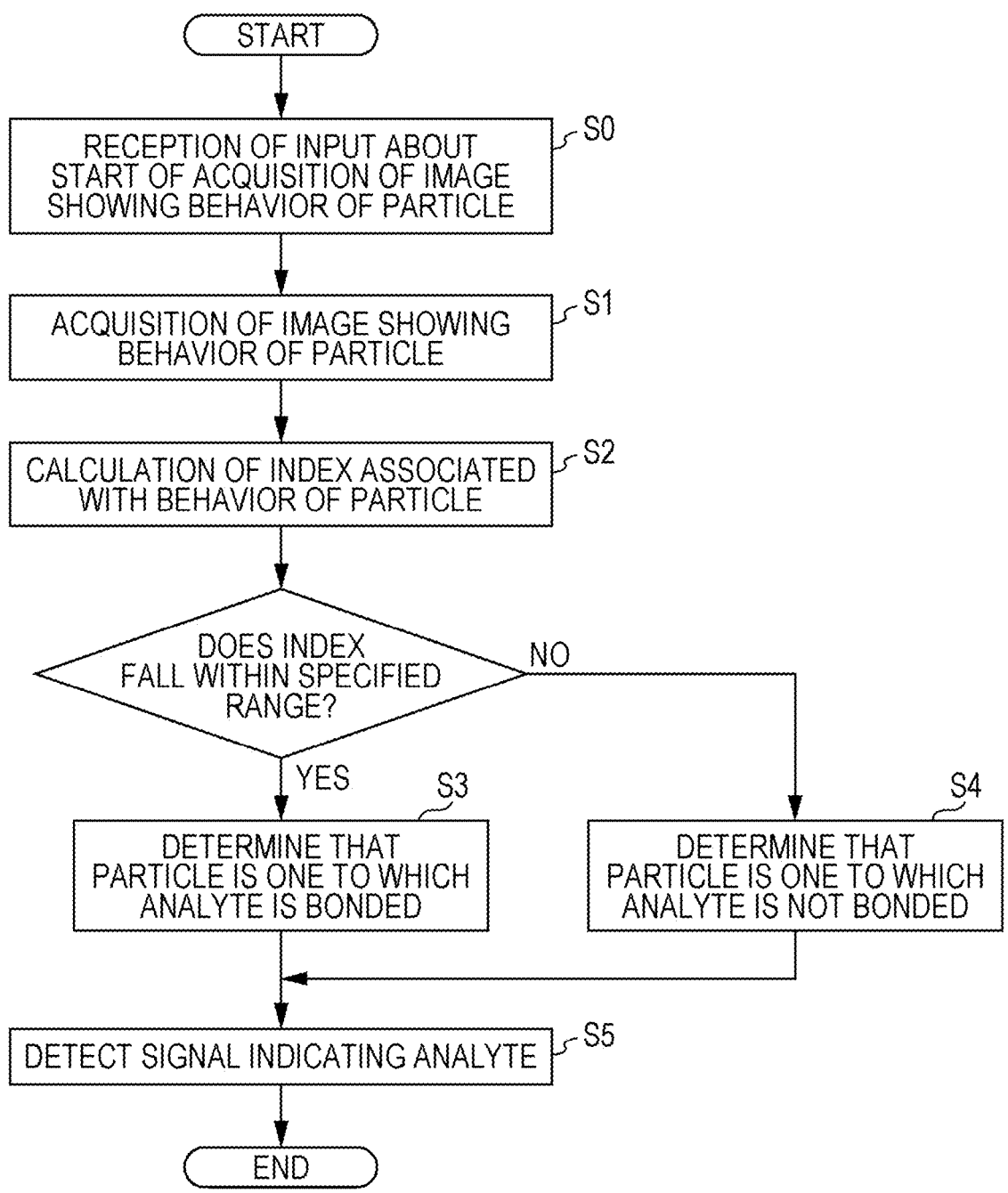
FIG. 5 is a diagram showing the operation of a processing unit.

Next, the operation of the detection device according to the present disclosure will be described with reference to FIG. 5. The operation of the detection device according to the present disclosure can be controlled by the processing unit (CPU) 30 in the computer system 3.

Firstly, the processing unit 30 receives an input toward the computer main body 3a, wherein the input is for starting the acquisition of optical information (e.g., an image showing a behavior of a particle) generated by the measurement device 2, and the acquisition is to be carried out from the input device 3b by an inspector (step S0).

Subsequently, the processing unit 30 acquires optical information, e.g., an image showing a behavior of a particle, which is produced by the measurement device 2 (step S1).

Subsequently, the processing unit 30 calculates an index associated with a behavior of a particle from images respectively showing the behaviors of at least two types of particles, wherein the images are obtained in step S1 (step S2). A particle of which the index associated with the behavior of the particle falls within a specified range is identified as a particle to which an analyte is bonded (step S3), and a particle of which the index associated with the behavior of the particle is out of the specified range is identified as a particle to which the analyte is not bonded (step S4).

The particle to which the analyte is bonded is detected as an analyte signal (step S5).

The processing unit 30 can output information obtained in steps S1 to S5 from the display unit 3c through the image output interface 37. The processing unit 30 may record the information on the recording medium 40 or the like.

Steps S1 to S5 can be executed by means of a computer program. The computer program may be stored in a hard disk, a semiconductor memory element such as a flash memory, or a storage medium such as an optical disk. The form of the recording of the program on the recording medium is not particularly limited, as long as the display device can read out the program. The storage on the recording medium is carried out preferably in a non-volatile manner.

EXAMPLES

Hereinbelow, the present invention will be described in detail with reference to examples. However, the present invention is not limited by these examples.

Example 1

Detection and Quantification of PSA

Example 1-1

Production of Antibody Linker-Modified fL Chamber Array Flow Cell

Figure 6:
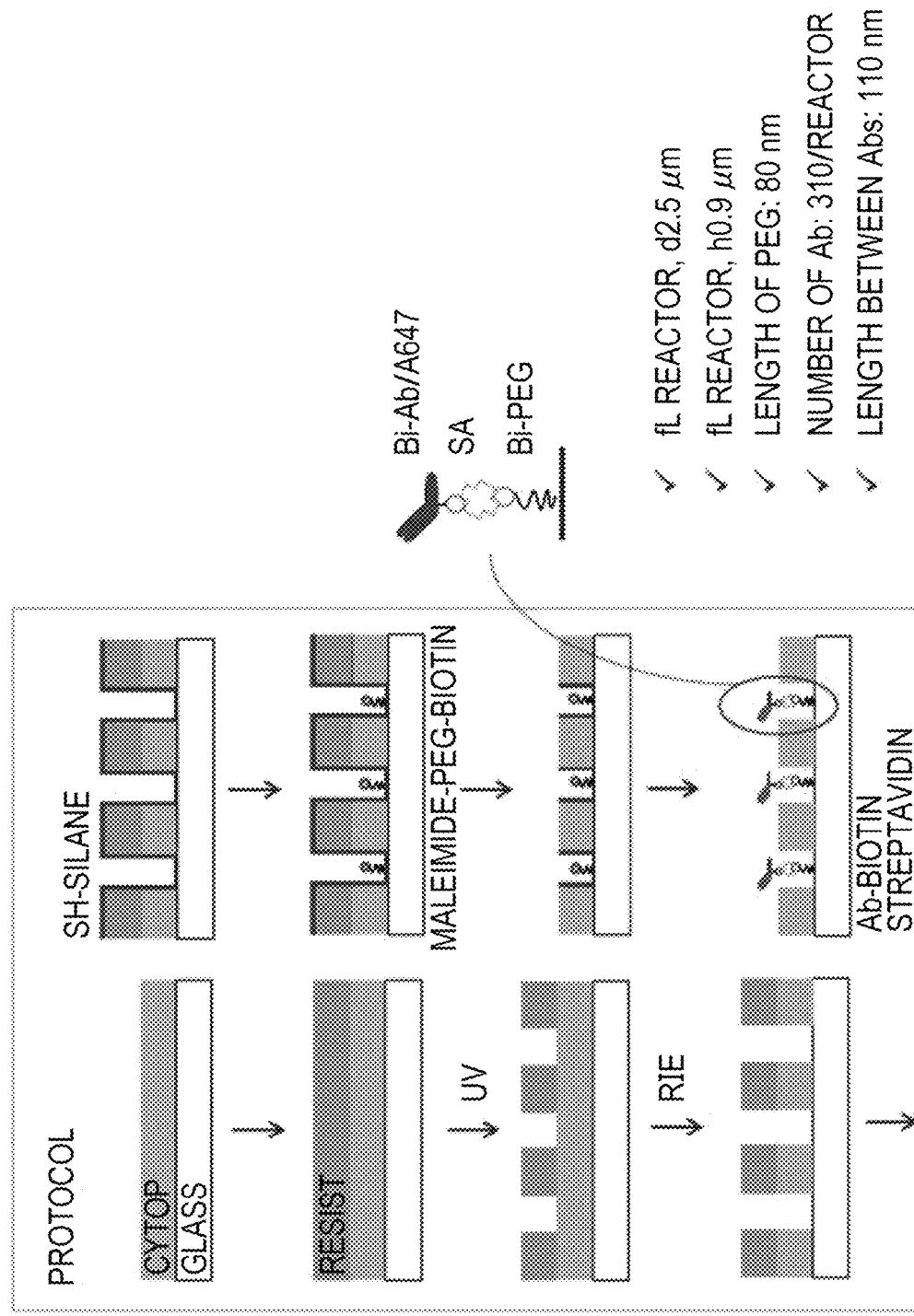
FIG. 6 is a schematic diagram illustrating the method for producing an antibody linker-modified fL chamber array flow cell (Example 1-1)

The production method is schematically shown in FIG. 6. The schematic illustration of the produced flow cell is shown in FIG. 7. Concretely, the flow cell was produced in the following manner.

Example 1-1-1

Application of CYTOP (Registered Trademark)

(1) A cover glass (Matsunami Glass Ind., Ltd.) was immersed in 8-N KOH and was then ultrasonically washed for 15 minutes.

(2) The cover glass was washed with running water and was then dried with a blower.

(3) The cover glass was set on a spin coater, and CYTOP (CTL-809M, AGC Inc.) was then dropped onto the cover glass. The spin coating was carried out in accordance with the following program. CYTOP was coated in such a manner that the depth of the chamber after the production became 0.8 µm.

TABLE 1

| | |
|---|---|
| slope | 5 s |
| 500 rpm | 10 s |
| slope | 5 s |
| 1900 rpm | 30 s |
| slope | 5 s |

(4) The coated cover glass was heated on a hot plate that had been heated to 180° C. for 1 hour.

Example 1-1-2

Photolithography (1) The CYTOP-coated glass was set on a spin coater, and a proper amount of a resist (AZ4903, Merck) was dropped onto the glass. The spin coating was carried out in accordance with the following program.

TABLE 2

| | |
|---|---|
| slope | 5 s |
| 500 rpm | 10 s |
| slope | 5 s |
| 7500 rpm | 30 s |
| slope | 5 s |

(2) The spin-coated glass was heated on a hot plate that had been heated to 55° C. for 3 minutes.

(3) The heated glass was heated on a hot plate that had been heated to 110° C. for 5 minutes.

(4) A Cr mask was set in an exposure device (Ba100it, San-ei Electric Co., Ltd.), and then the cover glass having the resist applied thereon was set in the exposure device. In the Cr mask, a plurality of regions, in each of which Cr was removed in a circle-like form so that the width (diameter) of the produced chamber became 2.5 µm, were formed.

(5) The mask was exposed to light at 256 W for 7 seconds.

(6) The resultant product was developed by immersing in a developing solution (AZ300MIF Developer, Merck) for 5 minutes.

(7) The developed product was washed with deionized water and was then dried with a blower.

Example 1-1-3

Etching (1) The washed cover glass was set in an etching device (RIE-10NR, Samco) and was etched in accordance with the following program.

TABLE 3

| $O_2$ | 50 sccm |
|---|---|
| Pressure | 10 Pa |
| Power | 50 W |
| Time | 4.5 min |

(2) The etched product was washed with deionized water.

Example 1-1-4

Modification with PEG Linker (1) The cover glass that had been pretreated was immersed in an SH organo silane (KBM-803, Shinetsu) solution for 2 hours to perform silanization.

(2) A 1-mg/mL biotinylated PEG (PG2-BNML-10k, Nanocos)/25 mM MES solution was prepared and was then added onto the pretreated cover glass. The resultant product was degassed on ice and was then allowed to leave at room temperature for 1 hour.

(3) The cover glass that had been allowed to leave was immersed in acetone and was then ultrasonically washed for 5 minutes to remove the resist.

(4) The cover glass was immersed in ethanol and was then ultrasonically washed for 5 minutes.

(5) The cover glass was immersed in pure water, was then ultrasonically washed for 5 minutes, and was then dried with a blower.

Example 1-1-5

Production of Upper Surface Glass (1) A glass was prepared by forming a plurality of holes each having a diameter of 1.2 mm on a glass having a size of 24 mm×32 mm×5 mm.

(2) CYTOP (CTL-809M, AGC Inc.) was dropped onto the glass and was then spin-coated at 1000 rpm for 30 seconds.

(3) The resultant glass was heated for 1 hour on a hot plate that had been heated to 180° C.

Example 1-1-6

Bonding of Antibody to PEG Linker-Modified Substrate (1) A double-sided adhesive tape (7602 #25, Teraoka Seisakusho Co., Ltd.) having a die-cut area having a size of 3 mm×20 mm formed therein was adhered onto the PEG linker-modified substrate, and then the upper surface glass was pressed against the double-sided adhesive tape to produce a flow cell.

(2) PBST (20 μL) was injected into the flow cell.

(3) A 10-ug/mL streptavidin (Thermofisher) solution in PBST (20 μL) was injected into the flow cell. The flow cell was allowed to leave at room temperature for 30 minutes.

(4) PBST (100 μL) was injected into the flow cell.

(5) A solution containing 1 μg/mL of a biotinylated antibody and 1% of BSA in PBST (20 μL) was injected into the flow cell. The flow cell was allowed to leave at room temperature for 1 hour. The antibody: an anti-PSA monoclonal antibody manufactured by Biospecific (Product No. A45170), biotinylation: a biotin labeling kit SH manufactured by DOJINDO.

(6) PBST (100 μL) was injected into the flow cell.

Example 1-2

Production of Antibody-Binding Magnetic Nanoparticle

Figure 8:
FIG. 8 is a schematic diagram of an antibody-binding magnetic nanoparticle produced in Example 1-2.

An antibody-binding magnetic nanoparticle was produced. The schematic lustration of the particle is shown in FIG. 8.

Example 1-2-1

Beads Preparation (1) A solution of COOH magnetic nanoparticles (JSR) each having a diameter of about 550 nm was fully stirred with a vortex, and then a portion (80 μL) was pipetted and was then subjected to BF separation.

(2) DMF (300 μL) was added to the solution, and the resultant solution was fully stirred with a vortex, and the resultant solution was treated with ultrasonic waves for 5 minutes.

(3) The solution was subjected to magnetism collection, and then the procedure (2) was carried out again. This cycle was repeated three times in total.

(4) Subsequent to the magnetism collection, DMF (160 μL) was added, and the resultant solution was treated with ultrasonic waves for 5 minutes.

Example 1-2-2

Activation with EDC and NHS (1) 1 M NHS was prepared in the following composition. EDC was weighed.

NHS (11.5 mg)+DMF (100 μL)

EDC (7.7 mg)

(2) 1M NHS (40 μL) was added to the beads solution (Example 1-2-1).

(3) The NHS-beads solution (200 μL) was added to the weighed EDC.

(4) The resultant solution was treated with ultrasonic waves for 5 minutes.

(5) The solution was stirred with a stirrer (output: 80%) at room temperature for 2 hours.

(6) The solution was subjected to BF separation.

(7) DMF (300 μL) was added to the solution, and then the resultant solution was treated with ultrasonic waves for 5 minutes.

(8) The cycle of (6) through (7) was repeated 5 times in total.

(9) The solution was transferred to a new tube.

(10) Methanol (300 μL) was added to the solution, and then the resultant solution was treated with ultrasonic waves for 5 minutes.

(11) The solution was subjected to BF separation.

Example 1-2-3

Immobilization of Antibody (1) 25 mM MES (50 μL) was added to the solution, and then the resultant solution was treated with ultrasonic waves for 5 minutes.

(2) An antibody solution (43 μL) was added to the solution. The solution was stirred with a stirrer (output: 80%) at 4° C. overnight. The antibody: anti-PSA monoclonal antibody manufactured by Biospecific (product No. A45160), formation of Fab fragment: digestion with pepsin, fractionation (3) The solution was subjected to BF separation.

(4) 50 mM Tris (300 μL) was added to the solution. The resultant solution was stirred with a stirrer (output: 80%) at room temperature for 15 minutes.

(5) The solution was subjected to BF separation.

(6) HISCL, R3 (a buffer solution) (Sysmex) (200 μL) was added to the solution, and then the resultant solution was vortexed.

(7) The solution was subjected to BF separation.

(8) The cycle of (6) through (7) was repeated 3 times in total.

(9) HISCL, R3 (a buffer solution) (Sysmex) (1 mL) was added to the solution.

Example 1-3

Detection and Analysis

Example 1-3-1

Samples

Non-contaminated samples respectively containing various concentrations of a PSA in PBS and contaminated samples respectively containing various concentrations of the PSA in plasma were prepared as follows.
 PSA: HISCL, PSA, C2 calibrator (Sysmex) 20 ng/ml
 PBS: a phosphate buffer solution
 Plasma: PSA-free human plasma (Sunfco Ltd.)
 The PSA was diluted with PBS or the plasma.
 The concentrations of the PSA in non-contaminated samples: 0, 0.08, 0.4, 2.0, 10 pg/mL
 The concentration of the PSA in contaminated samples: 0, 2.0, 10, 50 pg/mL Example 1-3-2

Microscope

The information about the microscope, the lens and the camera used are as follows.
 Microscope: Olympus inverted fluorescence microscope IX71
 Lens: UPlanApo, 40×, NA1.00 (Olympus)
 Camera: DMK23UX174 (Imagingsource)

Example 1-3-3

Measurement Procedure (1) An antibody-binding magnetic nanoparticle solution (40 μL) was mixed with a sample solution (20 μL). The antibody-binding magnetic nanoparticle solution (40 μL) contained $10^6$ particles. In this case, the average amount of PSA on the particles after the mixing are shown in the table below.

TABLE 4

| PSA (pg/mL) | 0.08 | 0.4 | 2 | 10 | 50 |
|---|---|---|---|---|---|
| λ | 0.002 | 0.11 | 0.54 | 2.7 | 13.6 |

(2) The solution was stirred at room temperature for 1 hour.

(3) The antibody linker-modified fL chamber array flow cell was set on a magnet, and then the whole volume of the mixed solution was added to the flow cell.

(4) Subsequently, an oil (Fluorinert FC-40, 3M) (20 μL) was allowed to flow to seal the chamber array with the oil.

Figure 9:
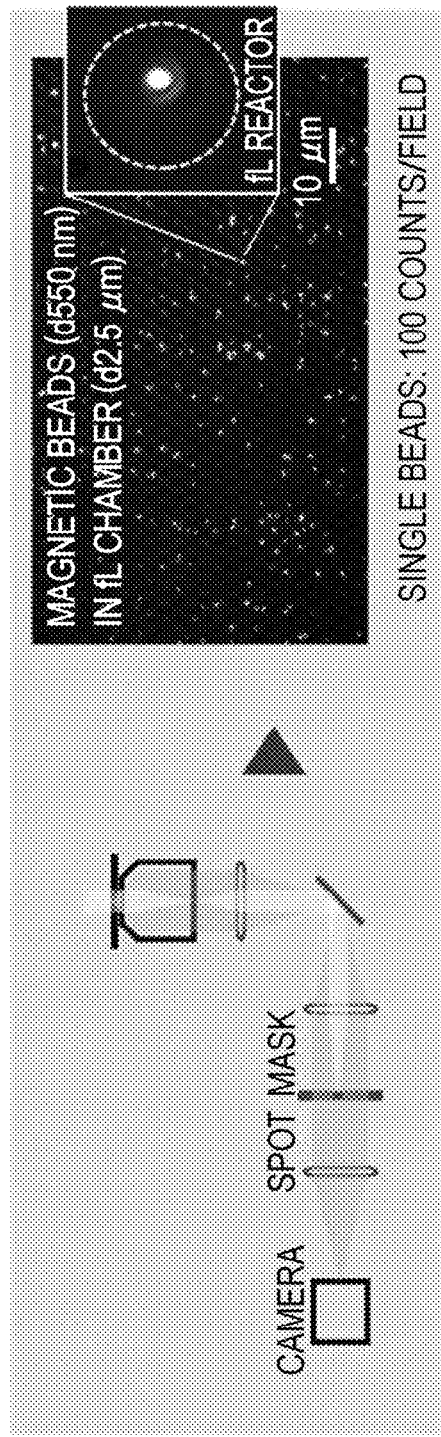
FIG. 9 is a diagram showing the schematic illustration of a dark-field image acquisition step in Example 1-3-3 and one example of an image acquired in the step.

(5) Immediately after the sealing, the flow cell was set on the microscope, and a dark field image was obtained in accordance with the procedure described in an already published document (T. Masaike et al, Nature structural & Molecular Biology, 15, 2008, 1326-1333) (50 fps for 1 sec, 20 fields were imaged). The time required from the addition of the mixture (the above-mentioned step (3)) till the acquisition of the image was about 3 minutes. The schematic illustration of this process is shown in FIG. 9.

Example 1-3-4

Figure 10:
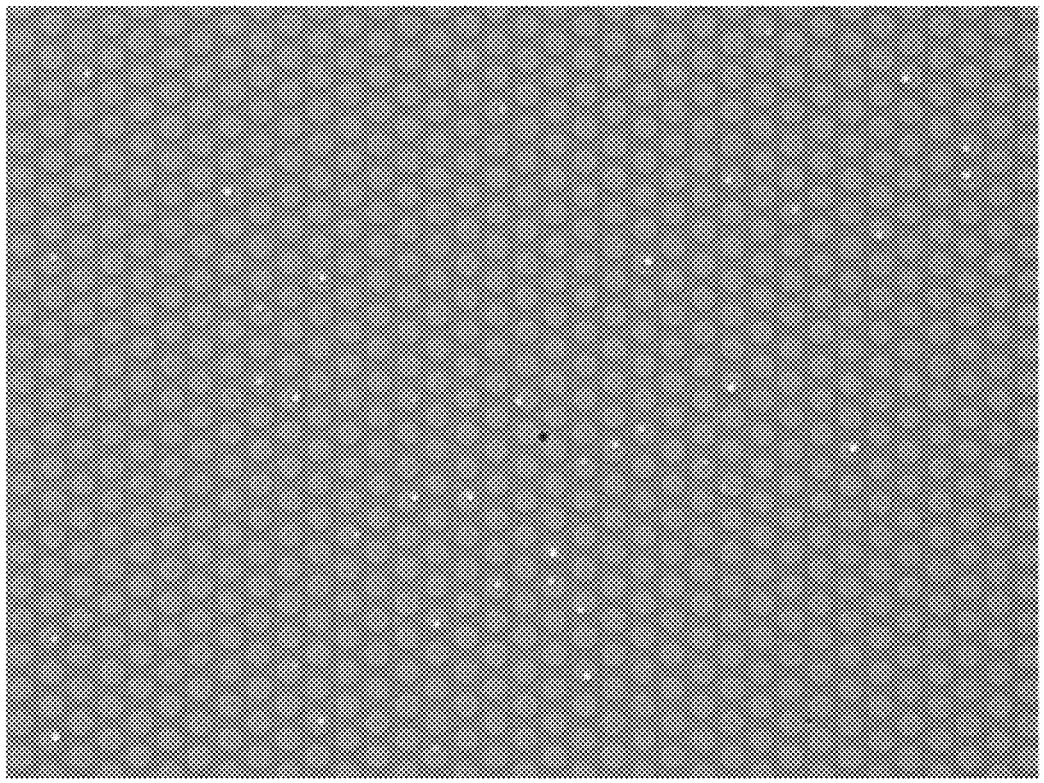
FIG. 10 is a diagram showing one example of an image acquired in the dark-field image acquisition step in Example 1-3-3.

Analysis (1) The acquired image was opened with Fiji (NIH). A part of the microscopic image is shown in FIG. 10. A state where nanoparticles are packed in the antibody linker-modified fL chamber array flow cell is observed.

(2) Subtract background was carried out to remove noises.

Figure 11:
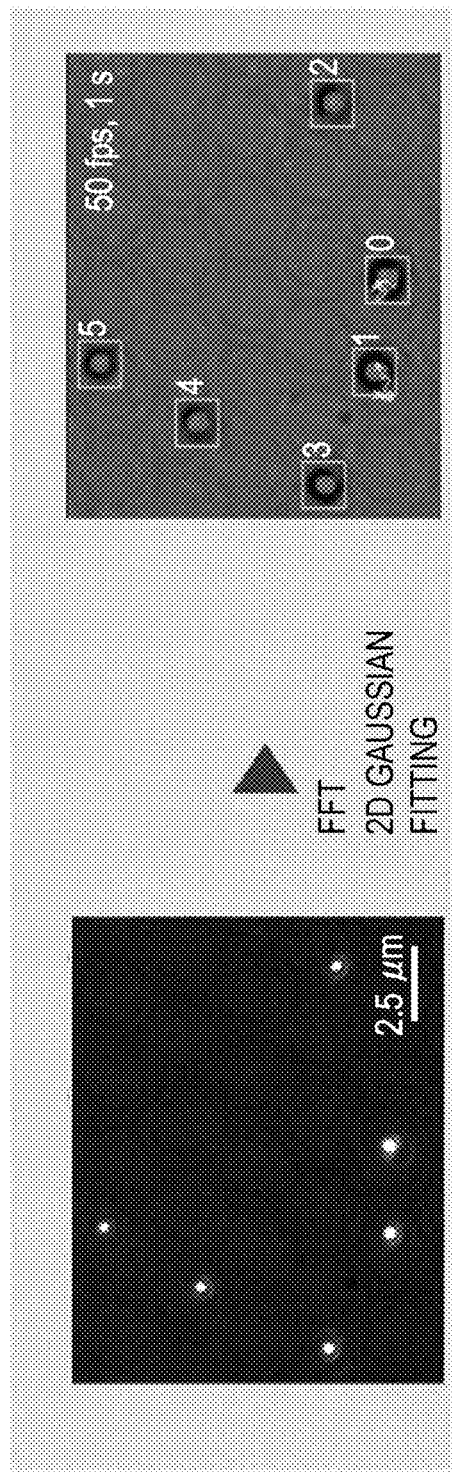
FIG. 11 is a diagram showing one example of an image which shows the time course of a coordinate of each particle and is acquired in Example 1-3-4.

(3) Track mate was booted to acquire the change in time of the coordinate of each particle. The schematic illustration of this process is shown in FIG. 11.

Figure 12A:
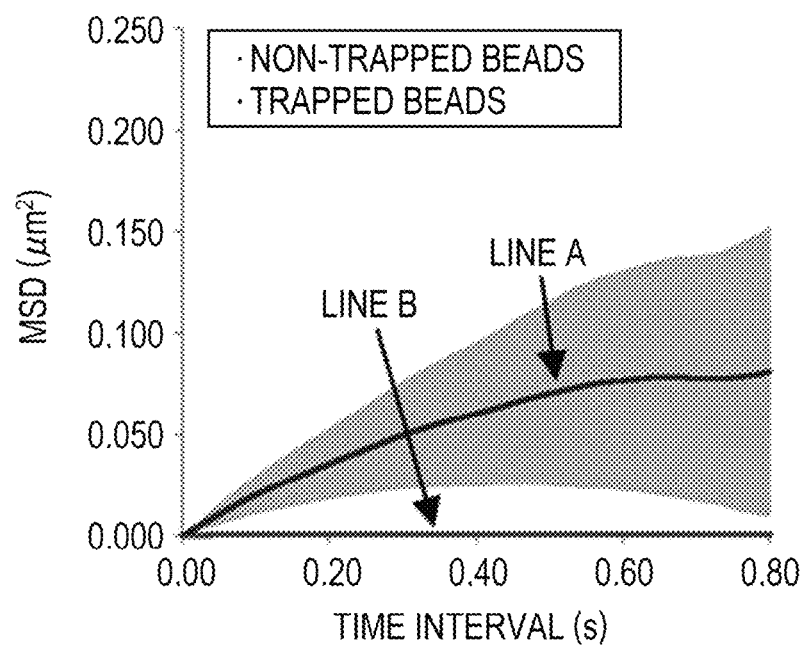
FIG. 12A is a graph showing the result obtained by calculating a mean square displacement (MSD) in accordance with Formula 1 from the time course of a coordinate of a nano-particle at the time point of the measurement of a PSA at 20 pg/mL in Example 1-3-4.
Figure 12B:
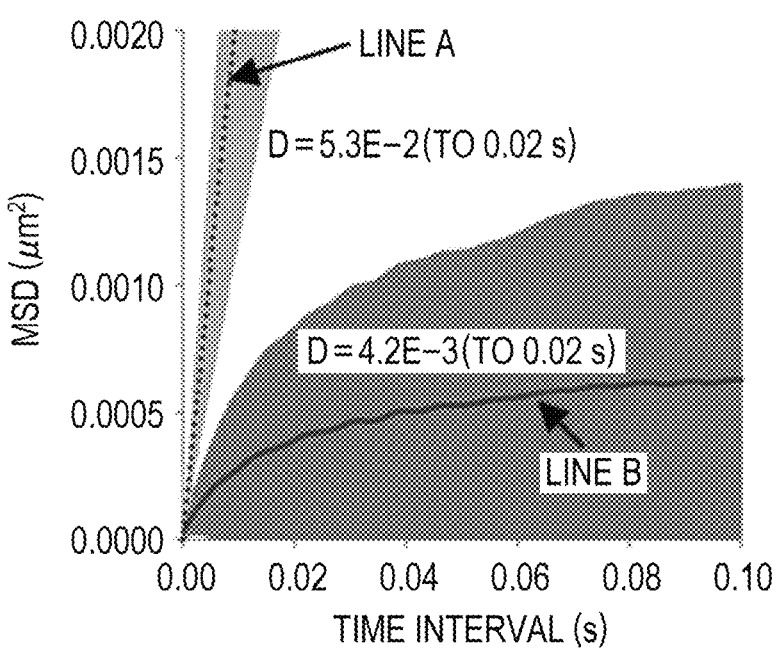
FIG. 12B is an enlarged view of the graph shown in FIG. 12A.

As one example, the result obtained by calculating a mean square displacement (MSD) in accordance with Formula 1 from the time course of a coordinate of each nano-particle in the measurement of a PSA at 20 pg/mL is shown in FIG. 12. In each of FIG. 12A and FIG. 12B, line A represents an MSD of a particle that was not trapped by the chamber array and line B represents an MSD of a particle that was trapped by the chamber array. FIG. 12B is an enlarged view of FIG. 12A, and demonstrates that the MSD of a particle trapped by the chamber array was saturated from the time point of 0.02 sec. onward.

[Mathematical formula 2]

$$MSD(dt) = \langle |r(t+dt) - r(t)|^2 \rangle \quad \text{(Formula 1)}$$
$$= \frac{1}{n}\sum |r(t+dt) - r(t)|^2$$

Subsequently, a diffusion coefficient D was calculated from the time course of the coordinate. More specifically, the diffusion coefficient (D) was calculated in accordance with Formula 2 from the tilt until the time point of 0.02 sec. The result of the determination of the distribution of D of the observed particles is shown in FIG. 13. The distribution shown in FIG. 13 was subjected to Gaussian fitting, and the occurrence of three distribution patterns was confirmed (a dashed line in FIG. 13). This fact demonstrates that the distribution is classified into a 3rd broad peak of particles that were not trapped by the chamber array and two peaks of particles that were trapped by the chamber array (1st peak and 2nd peak), and it is considered that the 1st peak corresponds to the particles which were trapped by the chamber array through non-specific adsorption and the 2nd peak corresponds to the tethered beads that trap the target through specific bonding.

[Mathematical formula 3]

$$D = \frac{1}{4}\frac{MSD(dt)}{dt} \quad \text{(Formula 2)}$$
$$= \frac{1}{4}\frac{1}{n \cdot dt}\sum |r(t+dt) - r(t)|^2$$
$$= \frac{1}{4}\sum |r(t+dt) - r(t)|^2$$

(5) Quantification of PSA

Figure 14:
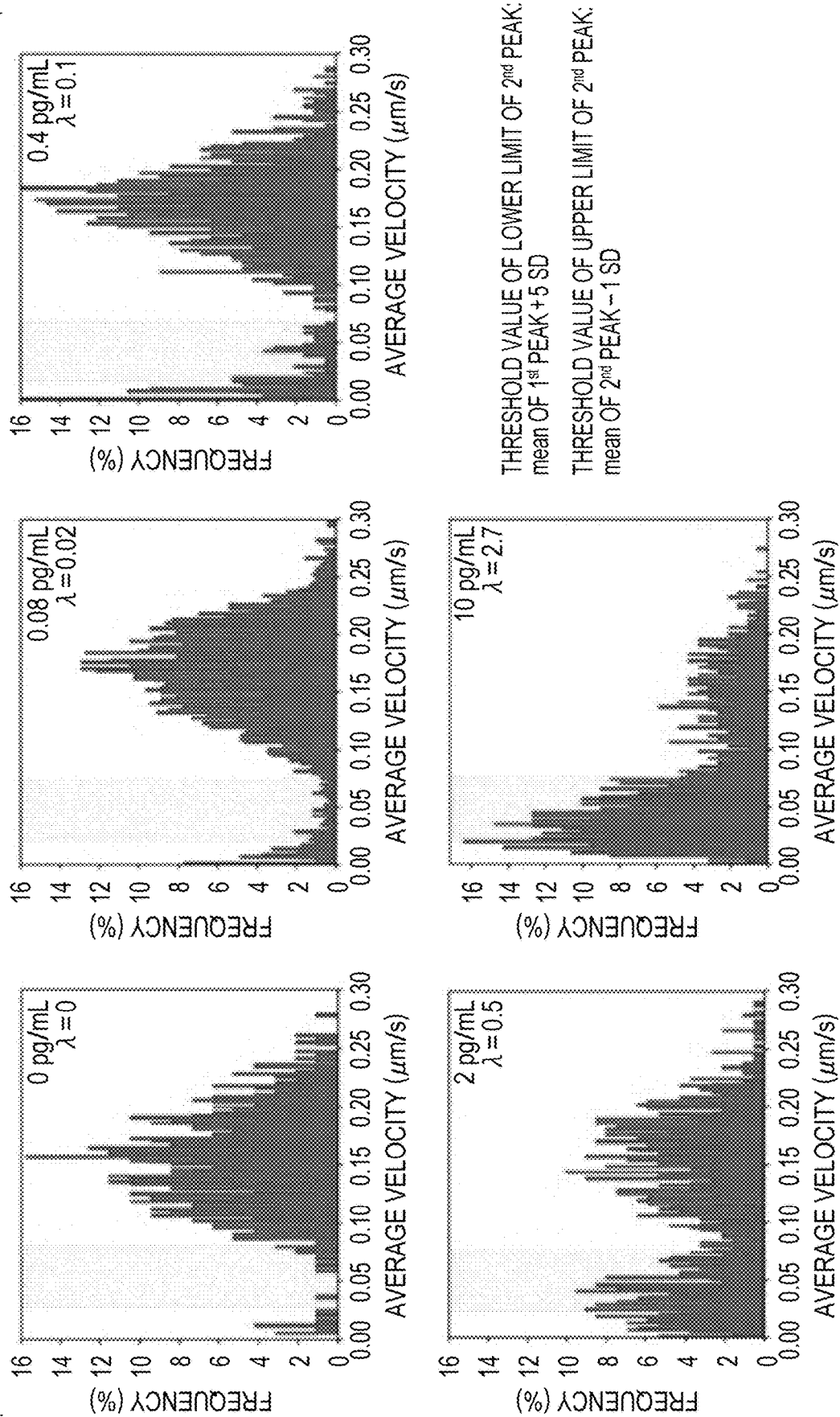
FIG. 14 illustrates graphs each showing the results of the counting of tethered beads corresponding to a $2^{nd}$ peak from data obtained from samples having various PSA concentrations with respect to a non-contaminated sample in Example 1-3-4.
Figure 15:
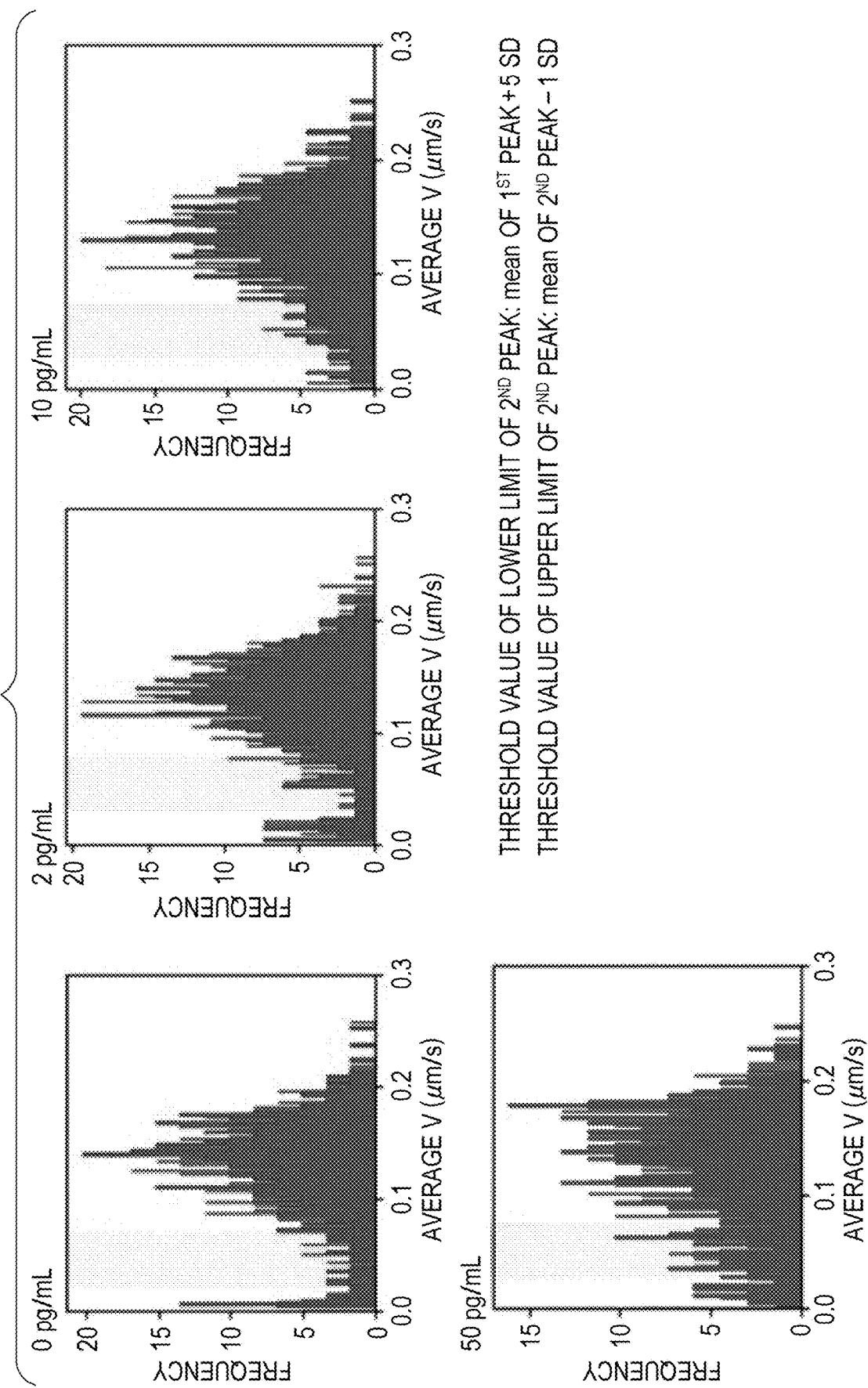
FIG. 15 illustrates graphs each showing the results of the counting of tethered beads corresponding to a $2^{nd}$ peak from data obtained from samples having various PSA concentrations with respect to a contaminated sample in Example 1-3-4.

The number of the tethered beads that corresponded to the 2nd peak was counted from the data obtained from samples having various PSA concentrations in the above-mentioned manner. The date obtained from the non-contaminated samples are shown in FIG. 14, and the data obtained from the contaminated samples are shown in FIG. 15. In this regard, a velocity (V) determined in accordance with Formula 3 below was employed as an index indicating a behavior of a particle.

[Mathematical formula 4]

$$V(dt) = \left\langle \frac{\sqrt{|r(t+dt) - r(t)|^2}}{dt} \right\rangle \quad \text{(Formula 3)}$$
$$= \frac{1}{n}\sum \frac{\sqrt{|r(t+dt) - r(t)|^2}}{dt}$$
$$= \frac{1}{n \cdot dt}\sum \sqrt{|r(t+dt) - r(t)|^2}$$
$$= \sum \sqrt{|r(t+dt) - r(t)|^2}$$

Figure 16:
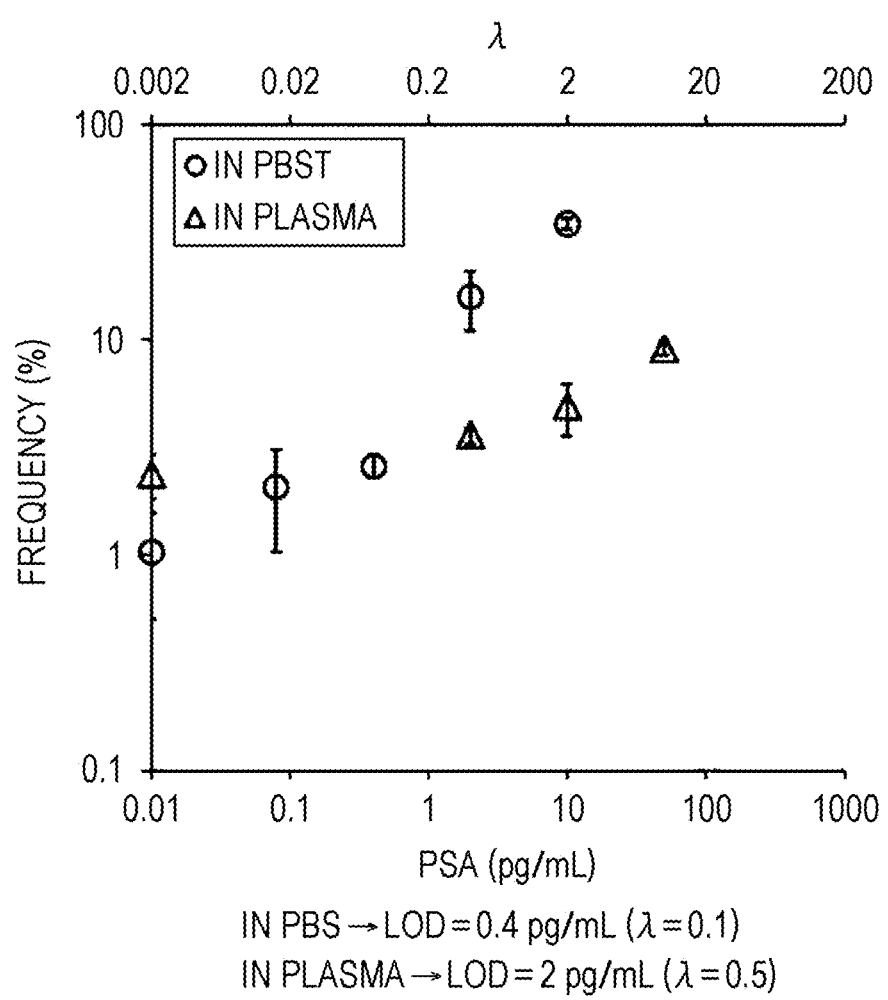
FIG. 16 is a graph showing the result of the change in concentration which is determined from the date of FIG. 14 and FIG. 15 with respect to each of the non-contaminated sample (in PBST) and the contaminated sample (in Plasma) in Example 1-3-4.

The result of the change in concentration, which was determined from the data obtained in FIG. 14 and FIG. 15, is shown in FIG. 16. In FIG. 16, circular plots represent the results of the measurement of the PSA added to PBS (non-contaminated samples), and triangular plots represent the results of the measurement of the PSA added to PSA-free human plasma (contaminated samples). The measurement was carried out immediately after the filling of the particle into the fL chamber. In both types of the samples, dependency on the concentration of the PSA was confirmed, and the detection lower limit in the non-contaminated samples was determined as 0.4 pg/mL and the detection lower limit in the contaminated samples was determined as 2 pg/mL. In the contaminated samples, the sensitivity was deteriorated. This is probably because the antigen-antibody reaction was inhibited by the plasma component.

What is claimed is:

1. An analyte detection method, comprising:
   a particle contact step of bringing an analyte in a sample of interest into contact with particles each capable of bonding to the analyte, whereby a portion of the particles bind to the analyte to form analyte-bonded particles and another portion of the particles do not bind to the analyte;
   a complex formation step of bringing the sample that had been subjected to the particle contact step into contact with a substrate onto which a trapping substance capable of bonding to the analyte is immobilized, whereby forming a complex of the analyte-bonded particles and the trapping substance on the substrate;
   a detection step of, subsequent to the complex formation step, detecting the analyte on the basis of an index associated with a behavior of the particle,
   wherein the trapping substance contains a linker,
   wherein the complex forming step is performed with external force drawing the particles to the substrate, and the detection step is performed without external force,
   wherein the index is the change in time of the coordinate of each particle on the basis of the Brownian motion, and
   wherein the detection step comprises measuring on the basis of the index: a particle non-specifically bound on the substrate; an analyte-bound particle on the substrate; and a particle in a free state without binding to the trapping substance.

2. The detection method according to claim 1, wherein a still image of the behavior of the particle is obtained or a moving image of the behavior of the particle is taken, and then the index associated with the behavior of the particle is determined on the basis of the still image or the moving image.

3. The detection method according to claim 2, wherein the analyte is detected by comparing a behavior pattern determined from the still image or the moving image with a predetermined behavior pattern of a complex containing the analyte and then determining whether or not the behavior pattern coincides with the behavior pattern of the complex containing the analyte.

4. The detection method according to claim 1, wherein the index is at least one index selected from the group consisting of a mean square displacement, a diffusion coefficient (D) and an average velocity (V).

5. The detection method according to claim 1, wherein the detection step comprises a step of determining that a particle of which the index associated with the behavior of the particle falls within a specified range is a particle to which the analyte is bonded.

6. The detection method according to claim 1, wherein the detection step comprises a step of determining that a particle of which the index associated with the behavior of the particle is equal to or less than the threshold value of the upper limit of the index or a particle of which the index is equal to or less than the threshold value of the upper limit of the index and is equal to or more than the threshold value of the lower limit of the index is a particle to which the analyte is bonded.

7. The detection method according to claim 1, wherein the detection step comprises a step of counting the number of particles to each of which the analyte is bonded and then quantifying the analyte on the basis of the result of the counting.

8. The detection method according to claim 1, wherein the linker is at least one substance selected from the group consisting of a nucleic acid, a polymeric substance and a lipid.

9. The detection method according to claim 1, wherein the length of the linker is 1 nm or longer.

10. The detection method according to claim 1, wherein the particle is a magnetic particle.

11. The detection method according to claim 1, wherein the particle has a particle size of 1 µm or less.

12. The detection method according to claim 1, wherein a chamber composed of a side surface and a bottom surface is formed on the substrate, wherein the tapping substance is immobilized on the bottom surface of the chamber and the complex is formed on the bottom surface of the chamber.

13. An analyte detection method, comprising steps of:
forming on a substrate a complex comprising an analyte in a sample of interest, particle capable of bonding to the analyte and a trapping substance capable of bonding to the analyte,
measuring: a particle non-specifically bound on the substrate; an analyte-bound particle on the substrate; and a particle in a free state without binding to the trapping substance, on the basis of at least one index selected from the group consisting of a mean square displacement, a diffusion coefficient (D) and an average velocity (V) of the Brownian motion of the particle, and
detecting the analyte in the analyte-bound particle on the substrate,
wherein the trapping substance contains a linker, and
wherein the complex forming step is performed with external force drawing the particles to the substrate, and the detection step is performed without external force.

14. An analyte detection method, comprising steps of:
forming on a substrate a complex comprising an analyte in a sample of interest, particle capable of bonding to the analyte and a trapping substance capable of bonding to the analyte,
taking a still image of the behavior of the particle or a moving image of the behavior of the particle,
calculating using the still image or the moving image at least one index selected from the group consisting of a mean square displacement, a diffusion coefficient (D) and an average velocity (V) of the Brownian motion of the particle,
measuring: a particle non-specifically bound on the substrate; an analyte-bound particle on the substrate; and a particle in a free state without binding to the trapping substance, on the basis of the index, and
detecting the analyte by determining the analyte-bound particle on the substrate,
wherein the trapping substance contains a linker, and
wherein the complex forming step is performed with external force drawing the particles to the substrate, and the detection step is performed without external force.

15. The detection method according to claim 1, wherein a value of the index for the particle in the free state without binding to the trapping substance is larger than a value of the index for the particle non-specifically bound on the substrate, and is larger than a value of the index for the analyte-bound particle on the substrate, and the value of the index for the analyte-bound particle on the substrate is larger than the value of the index for the particle non-specifically bound on the substrate.

16. The method according to claim 1, wherein the particles are magnetic particles and the external force is magnetic force.

* * * * *